United States Patent
Castleberry et al.

(10) Patent No.: US 11,590,240 B2
(45) Date of Patent: Feb. 28, 2023

(54) NANO-FIBULAR NANOPARTICLE POLYMER-DRUG CONJUGATE FOR SUSTAINED DERMAL DELIVERY OF RETINOIDS

(71) Applicant: Massachusetts Institute of Technology, Cambridge, MA (US)

(72) Inventors: Steven A. Castleberry, North Chicago, IL (US); Mohiuddin A. Quadir, Malden, MA (US); Paula T. Hammond, Newton, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 15/739,487

(22) PCT Filed: Jun. 23, 2016

(86) PCT No.: PCT/US2016/038953
§ 371 (c)(1),
(2) Date: Dec. 22, 2017

(87) PCT Pub. No.: WO2016/210087
PCT Pub. Date: Dec. 29, 2016

(65) Prior Publication Data
US 2018/0185513 A1 Jul. 5, 2018

Related U.S. Application Data

(60) Provisional application No. 62/183,431, filed on Jun. 23, 2015.

(51) Int. Cl.
| | |
|---|---|
| *A61K 47/69* | (2017.01) |
| *A61K 9/08* | (2006.01) |
| *A61K 9/06* | (2006.01) |
| *A61K 9/00* | (2006.01) |
| *A61K 31/203* | (2006.01) |
| *A61K 47/02* | (2006.01) |
| *A61K 47/58* | (2017.01) |

(52) U.S. Cl.
CPC ........ *A61K 47/6933* (2017.08); *A61K 9/0014* (2013.01); *A61K 9/06* (2013.01); *A61K 9/08* (2013.01); *A61K 31/203* (2013.01); *A61K 47/02* (2013.01); *A61K 47/58* (2017.08); *A61K 47/6907* (2017.08)

(58) Field of Classification Search
CPC ...... A61K 31/203; A61K 9/0014; A61K 9/06; A61K 47/58; A61K 47/6933; A61K 47/6907; A61P 17/06; A61P 17/10
See application file for complete search history.

(56) References Cited

U.S. PATENT DOCUMENTS

| | | | | |
|---|---|---|---|---|
| 4,021,573 A | * | 5/1977 | Lee | A61K 8/671 514/560 |
| 5,545,399 A | * | 8/1996 | Lee | A61K 8/347 424/59 |
| 2007/0010632 A1 | * | 1/2007 | Kaplan | A61L 17/005 525/423 |
| 2013/0012582 A1 | | 1/2013 | Crimi et al. | |

FOREIGN PATENT DOCUMENTS

JP 2005263669 * 9/2005 ......... A61K 31/7004

OTHER PUBLICATIONS

Zuccari et al. (Drug Delivery, 16:4 189-195 (Year: 2009).*
Singh (J. Chem. Soc. Perkin Trans II 1986 635-636) (Year: 1986).*
International Search Report and Written Opinion for International Application No. PCT/US2016/038953 dated Sep. 19, 2016.
Ku et al., "Synthesis and characterization of thermoresponsive polymeric nanoparticles," Biochip J, 8(1):8-14 (2014).
Wichit et al., "Polymeric micelles of PEG-PE as carriers of all-trans retinoic acid for stability improvement," AAPS PharmSciTech, 13(1):336-343 (2012).
Jenkins, A. D. et al., "Glossary of basic terms in polymer science (IUPAC Recommendations 1996)," Pure and Applied Chemistry, 68 (12):2287-2311 (1996).

* cited by examiner

*Primary Examiner* — Anna R Falkowitz
(74) *Attorney, Agent, or Firm* — Foley Hoag LLP; Alexander Akhiezer; Lawrence P. Tardibono

(57) ABSTRACT

Disclosed herein are conjugated polymers comprising a polymer and an all-trans retinoic acid (ATRA) prodrug covalently bound to the polymer by a hydrolysable linker L or a pharmaceutically acceptable salt thereof, and methods of using same to treat certain disorders. In an embodiment, the conjugated polymer comprises poly (vinyl alcohol) covalently bound to ATRA through an ester linkage.

21 Claims, 8 Drawing Sheets

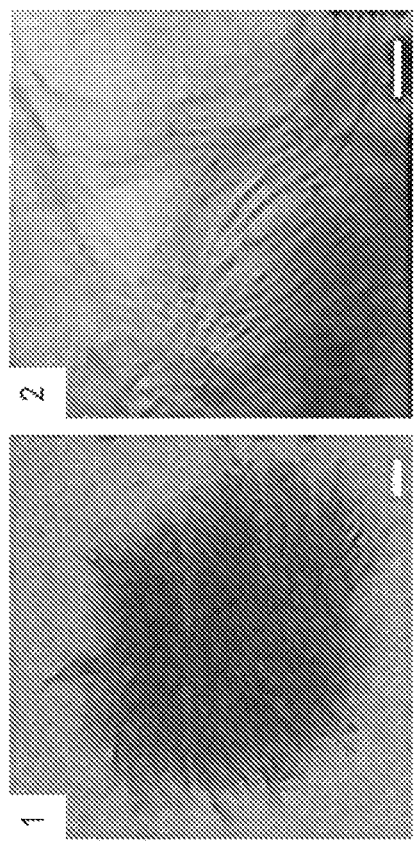
FIG. 3B
| Polymer (mg/mL) | ATRA (mg/mL) | Particle Diameter (nm) | Appearance |
|---|---|---|---|
| 100.0 | 2.45 | N/A | Opaque Yellow |
| 50.0 | 1.23 | 126.6 ± 4.1 | Clear Yellow |
| 25.0 | 0.61 | 131.1 ± 3.2 | Clear Yellow |
| 5.0 | 0.12 | 138.2 ± 5.1 | Clear Yellow |
| 1.0 | 0.02 | 148.1 ± 7.2 | Clear Light Yellow |
FIG. 3A
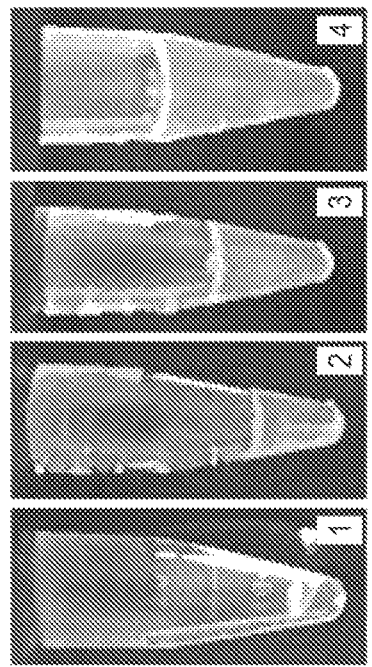
FIG. 3C
| Solvent | ATRA Solubility (mg/mL) | PATRA Solubility (mg/mL) |
|---|---|---|
| Hydroalcoholic | 0.67 ± 0.05 | 0.58 ± 0.07 |
| Water | < 0.01 | 0.33 ± 0.08 |
| PBS | < 0.01 | 0.35 ± 0.04 |
FIG. 3D

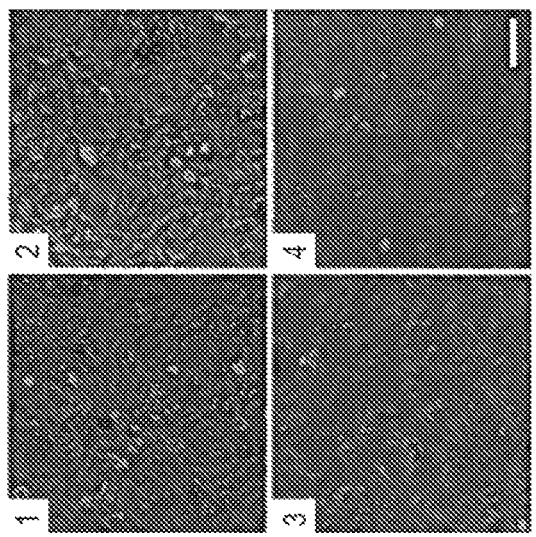
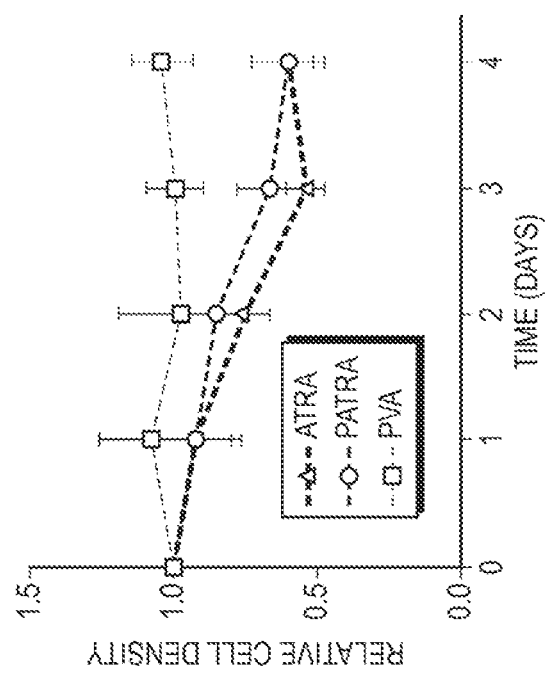
FIG. 5A
FIG. 5B

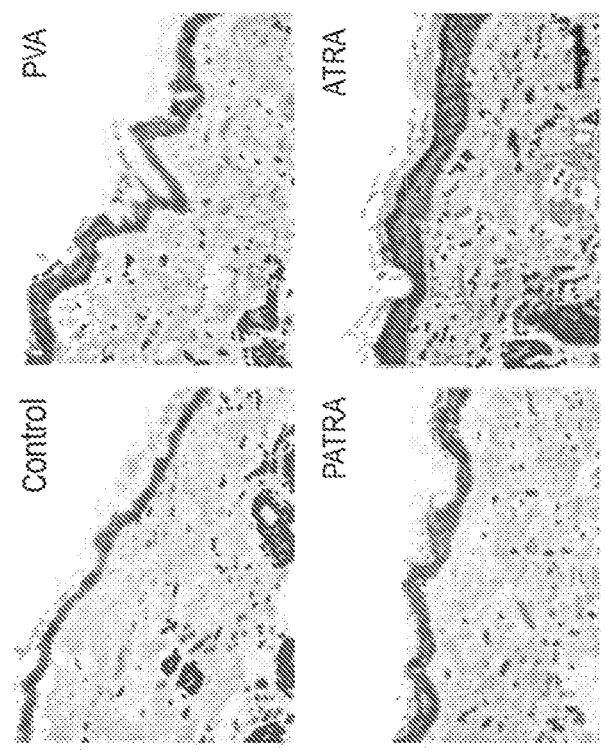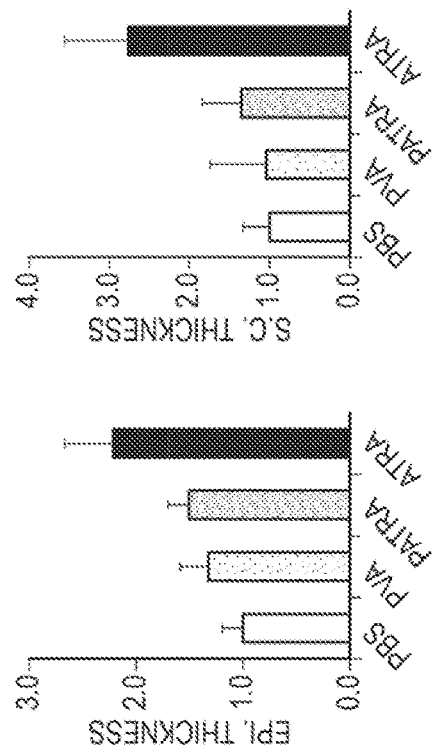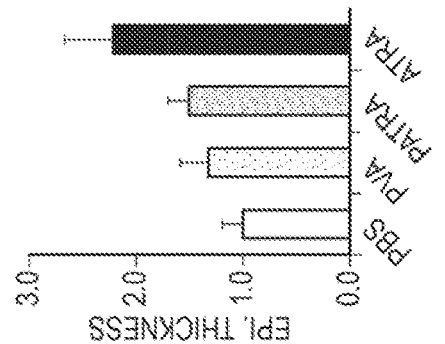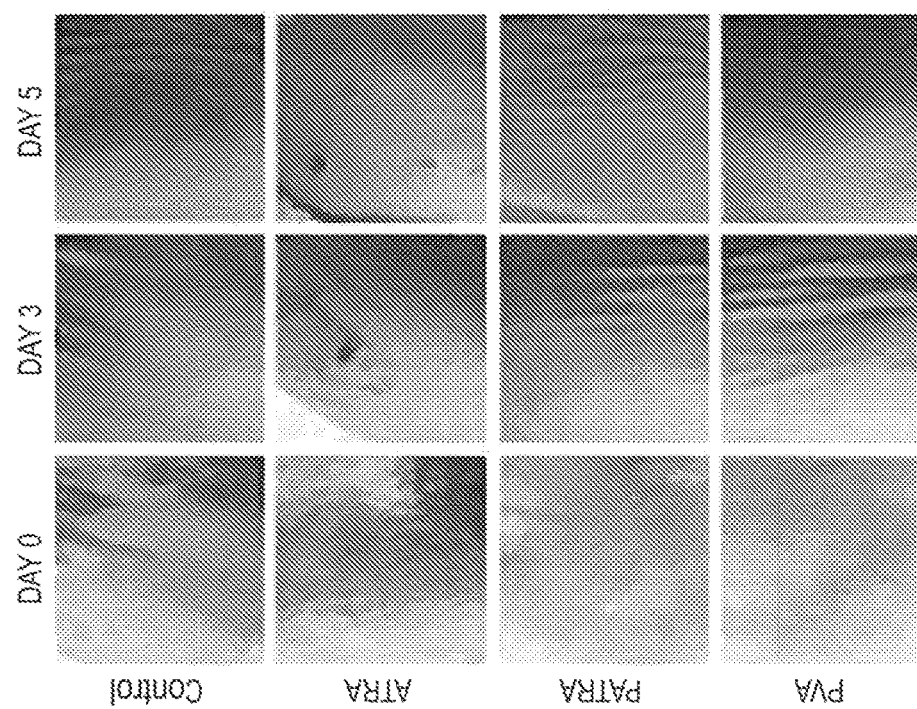

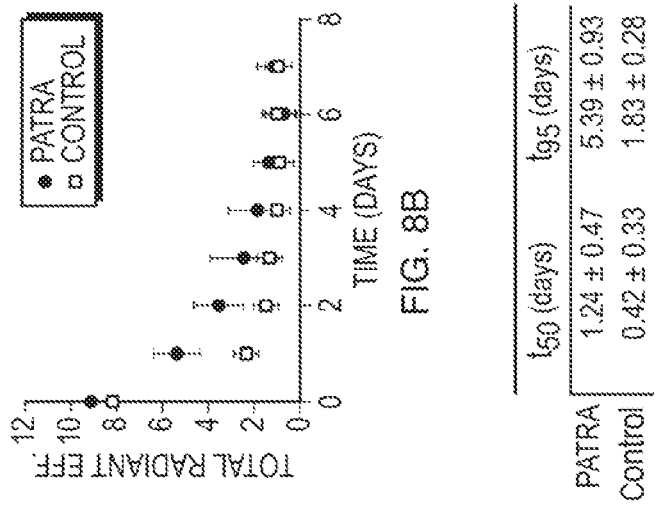
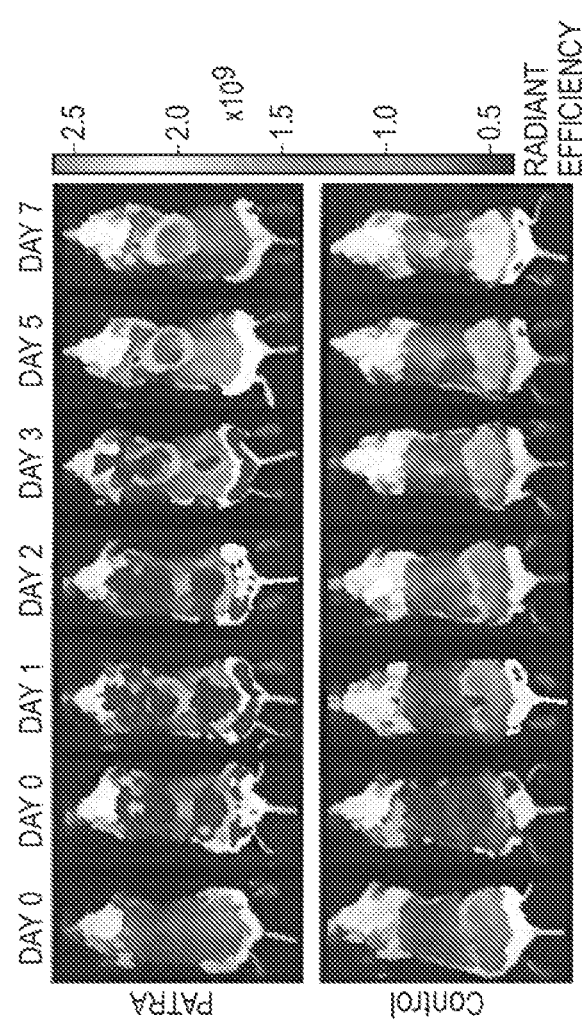
FIG. 8A
FIG. 8B
FIG. 8C

NANO-FIBULAR NANOPARTICLE POLYMER-DRUG CONJUGATE FOR SUSTAINED DERMAL DELIVERY OF RETINOIDS

RELATED APPLICATION

This application is the U.S. National Stage of International Application No. PCT/US2016/038953, filed Jun. 23, 2016, which designates the U.S., published in English, and claims the benefit of U.S. Provisional Application No. 62/183,431, filed on Jun. 23, 2015. The entire teachings of the above applications are incorporated herein by reference.

GOVERNMENT SUPPORT

This invention was made with Government support under Contract No. W911NF-07-D-0004 awarded by the Army Research Office. Additionally, this invention was made with Government support under the NCI Grant 2P30CA014051-39). The Government has certain rights in the invention.

BACKGROUND OF THE INVENTION

All-trans retinoic acid (ATRA), a derivative of vitamin A, is a common component in cosmetics and commercial acne creams as well as being a first-line chemotherapeutic agent. Today, formulations for the topical application of ATRA rely on creams and emulsions to incorporate the highly hydrophobic ATRA drug. These strategies, when applied to the skin, deliver ATRA as a single bolus which is immediately taken up into the skin and contributes to many of the known adverse side-effects of ATRA treatment, including skin irritation and hair loss. Existing pharmaceutical formulations of ATRA attempt to control these undesirable characteristics through controlled release formulations such as creams, microparticles, and emulsions. These strategies, however, rely on bolus delivery of active ATRA that, in the case of creams and emulsions, can become immediately available. This rapid increase in local concentration causes a number of adverse side-effects, while, on the other hand, microparticle approaches require injection across the dermis, increasing the potential for immunologic response and infection. The need exists for novel formulations of ATRA that would minimize its side effects.

SUMMARY OF THE INVENTION

The present invention is based on the discovery of a new ATRA derivative suitable for a topical delivery.

Accordingly, in an example embodiment, the present invention is a conjugated polymer comprising a polymer, and an all-trans retinoid acid (ATRA) prodrug covalently bound to the polymer by a hydrolysable linker L, or a pharmaceutically acceptable salt thereof. The polymer can comprise a repeat unit presented by structural formulas (I) or (II):

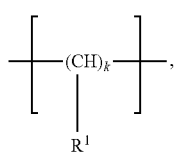

(I)

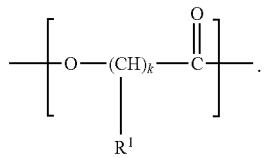

(II)

The ATRA prodrug can be represented by structural formula (III):

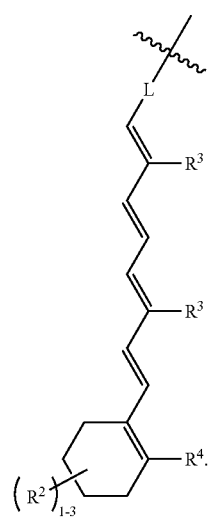

(III)

Hydrolysable linker L can include a substitutable atom of R1;

In structural formulas (I), (II), and (III), each $R^1$, independently, is $R^A$, a halogen, nitro, $-OR^A$, $-SR^A$, $-N(R^A)_2$, $-COOR^A$, $-OC(O)R^A$, $-C(O)R^A$, $-SO_4R^A$, $-PO_4(R^A)_2$, wherein $R^A$ is, for each occurrence independently, hydrogen, a C1-C6 alkyl, or a C6-C18 aryl, optionally substituted with one or more groups selected from $-OH$, $-NH_2$, a C1-C3 (di)alkylamino, a halogen, $-COOH$, a C1-C4 alkoxy, and phenoxy; $R^2$, $R^3$, and $R^4$, each independently, is a halogen, $-OH$, $-SH$, $-NH_2$, $-NO_2$, $-COOH$, $-NHR^B$, $-SO_4H$, $-PO_4H_2$, $-PO_4HR^B$, $R^B$, $-OR^B$, $-SR^B$, $-N(R^B)_2$, $-COOR^B$, $-OC(O)R^B$, $-C(O)R^B$, $-SO_4R^B$, $-PO_4(R^B)_2$; wherein $R^B$ is, for each occurrence independently, a C1-C6 alkyl or a C6-C18 aryl, optionally substituted with one or more groups selected from $-OH$, $-NH_2$, a C1-C3 (di)alkylamino, a halogen, COOH, a C1-C4 alkoxy, and phenoxy; and each k, independently, is 1-6.

In an example embodiment of the invention, by covalently bonding the ATRA moiety through a hydrolytically degradable ester linkage to a hydrophilic polymer PVA, an amphiphilic nanomaterial is created that is water soluble. This material acts as a pro-drug and accumulates within the site of deliver (e.g., skin) to allow for the sustained controlled delivery of the active pharmaceutical ingredient (ATRA). The experiments disclosed herein demonstrated a release of active ATRA for 10 days in vitro, while significantly enhancing dermal accumulation of the ATRA in explant pig skin. In vivo, the pro-dug formulation reduces application site inflammation compared to free ATRA and retains the drug at the application site at measurable quantities for up to six days.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 3 illustrates the results of nano-fiber PATRA solubility analysis and characterization: (A) Characterization of particle size and solution appearance for different concentrations of PATRA in water; (B) TEM images of nano-fiber PATRA formed in water (PATRA forms thin (3-5 nm) fibers (2) that agglomerate into nanoparticles (1)); (C) Digital images of solubilization of PATRA dry powder (1) at 50 mg/mL (2), 25 mg/mL (3), and 5 mg/mL (4) concentrations; and (D) Solubility of ATRA and PATRA in different solutions (data shown is mean±S.D., n=3).

FIG. 5 presents the results of comparison of impact of ATRA and PATRA on cell viability. (A) Relative cell density of cell cultures treated with ATRA, PATRA, or PVA. ATRA in-well concentration was set at 10 µM and PATRA concentration was set at an equivalent ATRA concentration. The concentration of PVA was determined by the PVA concentration in PATRA treated wells. (B) Brightfield imaging after four days in culture of NIH-3T3 cells that are either untreated (1) or treated with (2) PVA, (3) PATRA, (4) ATRA. Scale bar=50 µm (data shown is mean±S.D., n=5).

FIG. 7 presents the results of examination of a reaction to ATRA application to the dermis: (A) Digital imaging of mouse dermis 0, 3, and 5 days post-application; (B) Histological sections of treated mouse dermis (changes in epidermal and stratum corneum thickness are clearly observed due to bolus administration of ATRA; these changes are not observed in other treatment groups); (C) and (D) Quantification of histological findings for the treatment groups after five days (data shown are mean±S.D., n=4).

FIG. 8 presents the results of investigating retention of PATRA in the skin of mice: (A) IVIS imaging of fluorescently labeled PATRA over 7 days (unconjugated dye is seen to disappear after only two days while PATRA conjugated dye stays for up to 5 days; material was added at two locations on the midline of the backs of mice); (B) Quantification of total radiant efficiency for each application site for PATRA and dye treated mice; (C) Half-life and $t_{95}$ measured from first-order exponential fits of fluorescent data (data shown is mean±S.D., n=6).

Figure 1:
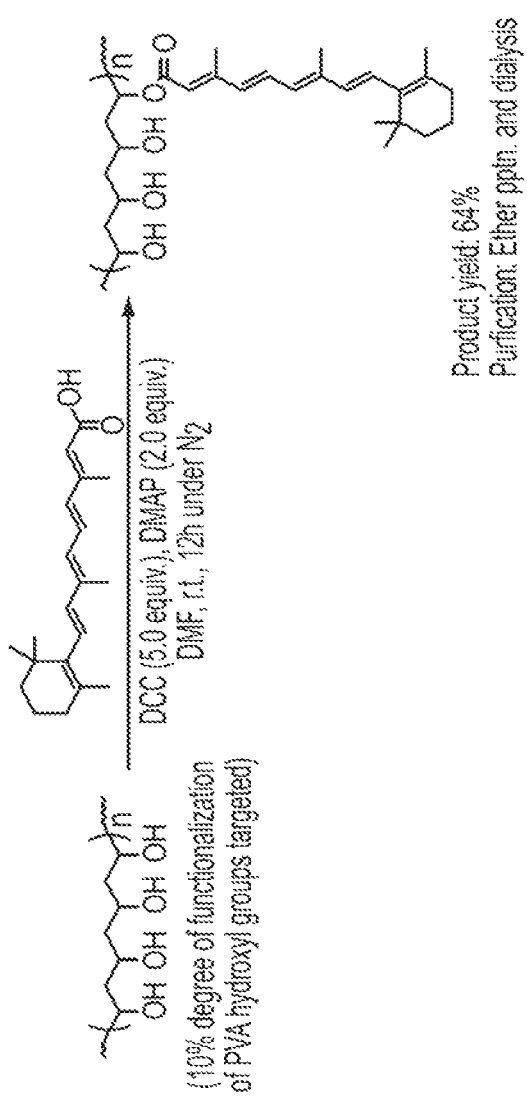
FIG. 1 illustrates a synthetic scheme employed to covalently link ATRA to PVA to produce an example embodiment of a conjugated polymer of the present invention.

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

DETAILED DESCRIPTION OF THE INVENTION

A description of example embodiments of the invention follows.

"Alkyl" means a saturated aliphatic branched, cyclic or straight-chain monovalent hydrocarbon radical having the specified number of carbon atoms. For example, "$(C_1-C_6)$ alkyl" means a radical having from 1-6 carbon atoms in a linear or branched arrangement. "$(C_1-C_6)$alkyl" includes methyl, ethyl, propyl, butyl, pentyl, and hexyl. Also included within the definition of "alkyl" are those alkyl groups that are optionally substituted. Suitable substitutions include, but are not limited to, halogen, —OH, —CN, alkoxy, amino, cycloalkyl, aryl, heteroaryl, or aryloxy.

"Aromatic," used alone or as part of a larger moiety as in "aralkyl," "aralkoxy," or "aryloxyalkyl," includes carbocyclic aromatic rings and heteroaryl rings. The term "aromatic group" may be used interchangeably with the terms "aryl," "aryl ring," "aromatic ring," and "aryl group." Many aromatic groups are planar, cyclic groups having conjugated π-orbitals where the number of π electrons obeys the formula 4n+2, where n is an integer.

"Aryl" means an aromatic monocyclic, or polycyclic hydrocarbon ring radical. Aryl systems include, but are not limited to, phenyl, naphthalenyl, fluorenyl, indenyl, azulenyl, and anthracenyl. Also included within the definition of "aryl" are those aryl groups having an optionally substituted carbon atom. Suitable substitutions include, but are not limited to, alkyl, cycloalkyl, alkoxy, halogen, amino, —OH, —CN, —NO$_2$, —SO$_3$H.

"Hetero" refers to the replacement of at least one carbon atom member in a ring system with at least one heteroatom selected from N, S, and O. A hetero ring may have 1, 2, 3, or 4 carbon atom members replaced by a heteroatom. When the heteroatom is N, the N-atom can be substituted with H, alkyl, cycloalkyl, cycloalkylalkyl, aryl, arylalkyl, heteroaryl, heteroarylalkyl (preferably, —H, $(C_1-C_6)$alkyl, halo$(C_1-C_6)$ alkyl or $(C_1-C_3)$alkylcarbonyl), each of which can be optionally substituted with halogen, hydroxy, alkoxy, haloalkyl, alkyl, etc. When the heteroatom is S, it can be optionally mono- or di-oxygenated (i.e. —SO)— or —S(O)$_2$—).

"Heteroaryl" means a heteroaromatic monocyclic or polycylic ring radical. Heteroaryl rings are 5- and 6-membered aromatic heterocyclic rings containing 1 to 4 heteroatoms independently selected from N, O, and S, and include, but are not limited to furan, thiophene, pyrrole, imidazole, pyrazole, oxazole, isoxazole, thiazole, isothiazole, 1,2,3-triazole, 1,2,4-triazole, 1,3,4-oxadiazole, 1,2,5-thiadiazole, 1,2,5-thiadiazole 1-oxide, 1,2,5-thiadiazole 1,1-dioxide, 1,3,4-thiadiazole, pyridine, pyridine-N-oxide, pyrazine, pyrimidine, pyridazine, 1,2,4-triazine, 1,3,5-triazine, and tetrazole. Bicyclic heteroaryl rings are bicyclo[4.4.0] and bicyclo[4.3.0] fused ring systems containing 1 to 4 heteroatoms independently selected from N, O, and S, and include indolizine, indole, isoindole, benzo[b]furan, benzo[b]thiophene, indazole, benzimidazole, benzthiazole, purine, 4H-quinolizine, quinoline, isoquinoline, cinnoline, phthalazine, quinazoline, quinoxaline, 1,8-naphthyridine, and pteridine. Also included within the definition of "heteroaryl" are those heteroaryl groups having an optionally substituted carbon atom. Suitable substitutions include, but are not limited to, alkyl, cycloalkyl, alkoxy, halogen, amino, —OH, —CN, —NO$_2$, —SO$_3$H. Additionally, the heteroatom can be substituted, as defined above for "hetero."

"Halogen" used herein refers to fluorine, chlorine, bromine, or iodine.

"Haloalkyl" and "halocycloalkyl" include mono, poly, and perhaloalkyl groups where the halogens are independently selected from fluorine, chlorine, and bromine. The alkyl portion can be as defined above for "alkyl," including its substituents.

"Alkoxy" means an alkyl radical attached through an oxygen linking atom, such as alkyl-O—. For example, "(C$_1$-C$_4$)-alkoxy" includes methoxy, ethoxy, propoxy, and butoxy. The alkyl portion can be as defined above for "alkyl," including its substituents.

"Aryloxy" means an aryl radical attached through an oxygen linking atom, such as aryl-O—. The aryl portion can be as defined above for "aryl," including its substituents. An example of an aryloxy radical is phenoxy group.

"Heteroaryloxy" means a heteroaryl radical attached through an oxygen linking atom, such as heteroaryl-O—. The heteroaryl portion can be as defined above for "heteroaryl," including its substituents.

"Heterocyclyl" means an optionally substituted, saturated or unsaturated, nonaromatic cyclic radical, which has at least one heteroatom in at least one carbon atom-containing ring. Each ring of the heterocyclic group containing a heteroatom may have 1, 2 or 3 heteroatoms. Suitable substitutions on alkyl carbon atoms include, but are not limited to, halogen, —OH, —CN, alkoxy, amino, cycloalkyl, aryl, heteroaryl, or aryloxy. Suitable substitutions on aryl carbon atoms include, but are not limited to, alkyl, cycloalkyl, alkoxy, halogen, amino, —OH, —CN, —NO$_2$, —SO$_3$H. When the heteroatom is N, it can be substituted with H, alkyl, cycloalkyl, cycloalkylalkyl, aryl, arylalkyl, heteroaryl, heteroarylalkyl (preferably, —H, (C$_1$-C$_6$)alkyl, halo(C$_1$-C$_6$)alkyl or (C$_1$-C$_3$)alkylcarbonyl), each of which can be optionally substituted with halogen, hydroxy, alkoxy, haloalkyl, alkyl, etc. When the heteroatom is S, it can be optionally mono- or di-oxygenated (i.e. —S(O)— or —S(O)$_2$—).

"Amino" means —NH$_2$; "alkylamine" and "(di)alkylamine" mean —NHR and —NR$_2$, wherein R is an alkyl group.

"All-trans retinoic acid" or "ATRA" refers to a compound of the following structural formula:

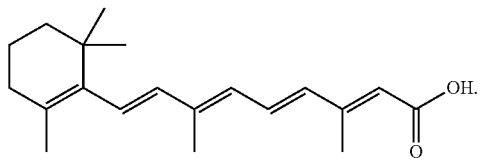 [SMILES: CC1=C(/C=C/C(C)=C/C=C/C(C)=C/C(=O)O)C(C)(C)CCC1]

As used herein, the term "hydrolysable linker" refers to a bivalent radical that connects two chemical moieties via a covalent bond and that is chemically labile to a hydrolysis reaction at physiological pH and temperature. For example, an ester formed by one of the hydroxyl groups of a polyvinyl alcohol (PVA) and the carbonyl carbon of an ATRA molecule is a hydrolysable linker —C(O)O—. Where one of the moieties connected via a hydrolysable linker is an active pharmaceutical ingredient (API), such as ATRA, suitable linkers include those that do not substantially reduce the activity of the API. In example embodiments, a linker is a chemically and biologically inert. Examples of linkers include any one of the chemical moiety L, described below. In example embodiment, the hydrolysable linker L includes a substitutable atom of the polymer chain or a pendant group on the polymer chain, as described below.

"Prodrug" means a pharmaceutically acceptable form of an API or an effective derivative of an API (or a salt thereof), wherein the prodrug may be: 1) a relatively active precursor which converts in vivo to the API; 2) a relatively inactive precursor which converts in vivo to the API; or 3) a relatively less active component of the compound that contributes to therapeutic activity after becoming available in vivo (e.g., as a metabolite). See "Design of Prodrugs", ed. H. Bundgaard, Elsevier, 1985. For example, an ATRA-polymer conjugate described herein is a prodrug of ATRA, where ATRA becomes available in vivo upon hydrolysis of the hydrolysable linker L.

"Substitutable atom" means any atom of a chemical moiety available for a formation of a covalent bond with another moiety. Examples of substitutable atoms include carbon, oxygen, nitrogen, and sulfur, without limitation. In an example embodiment, where a hydroxyl group of the PVA forms an ester moiety with the carbonyl carbon of an ATRA molecule, the oxygen of the hydroxyl is a substitutable atom.

"Polymer functionalization" means introduction of chemical groups into a polymer molecule or conversion of one chemical group to another group, which leads to a polymer with chemical, physical, biological, pharmacological, or other functions. Polymer functionalization can be quantified by determining a percentage of the chemical groups of a given type being introduced or converted (functionalized). For example, where the polymer is PVA, and about one tenth of the pendant hydroxyl groups are functionalized by covalent attachment to an ATRA prodrug via a hydrolysable linker L, the functionalization of PVA is about 10%.

"Subject" and "patient" may be used interchangeably, and they mean a mammal in need of treatment, e.g., companion animals (e.g., dogs, cats, and the like), farm animals (e.g., cows, pigs, horses, sheep, goats and the like) and laboratory animals (e.g., rats, mice, guinea pigs and the like). Typically, the subject is a human in need of treatment.

"Treating" or 'treatment" means obtaining a desired pharmacological and/or physiological effect. The effect can be prophylactic or therapeutic, which includes achieving, partially or substantially, one or more of the following results: partially or totally reducing the extent of the disease, disorder or syndrome; ameliorating or improving a clinical symptom or indicator associated with the disorder; delaying, inhibiting or decreasing the likelihood of the progression of the disease, disorder or syndrome; or partially or totally delaying, inhibiting or reducing the likelihood of the onset or development of disease, disorder or syndrome.

The term "treat" means decrease, suppress, attenuate, diminish, arrest, or stabilize the development or progression of a disease (e.g., a disease or disorder delineated herein), lessen the severity of the disease or improve the symptoms associated with the disease.

"Metabolite" means a pharmaceutically acceptable form of a metabolic derivative of a compound (or a salt thereof) of the invention, wherein the derivative is an active compound that contributes to therapeutic activity after becoming available in vivo.

"Effective amount" means that amount of active compound agent that elicits the desired biological response in a subject. Such response includes alleviation of the symptoms of the disease or disorder being treated. The effective amount of a compound of the invention in such a therapeutic method is from about 0.01 mg/kg/day to about 1000 mg/kg/day, from about 0.1 mg/kg/day to about 100 mg/kg/day, from about 0.5 mg/kg/day to about 50 mg/kg/day, or from about 1 mg/kg/day to 10 mg/kg/day.

"Pharmaceutically acceptable carrier" means compounds and compositions that are of sufficient purity and quality for use in the formulation of a composition of the invention and that, when appropriately administered to an animal or human, do not produce an adverse reaction.

"Disease" means any condition or disorder that damages or interferes with the normal function of a cell, tissue, or organ.

The term "compound," when referring to a conjugated polymer of this invention, refers to a collection of molecules having an identical chemical structure, except that there may be isotopic variation among the constituent atoms of the molecules. Thus, it will be clear to those of skill in the art that a compound represented by a particular chemical structure containing indicated deuterium atoms, will also contain lesser amounts of isotopologues having hydrogen atoms at one or more of the designated deuterium positions in that structure. The relative amount of such isotopologues in a compound of this invention will depend upon a number of factors including the isotopic purity of deuterated reagents used to make the compound and the efficiency of incorporation of deuterium in the various synthesis steps used to prepare the compound. However, as set forth above the relative amount of such isotopologues in toto will be less than 49.9% of the compound. In other embodiments, the relative amount of such isotopologues in toto will be less than 47.5%, less than 40%, less than 32.5%, less than 25%, less than 17.5%, less than 10%, less than 5%, less than 3%, less than 1%, or less than 0.5% of the compound.

The invention also provides salts of the conjugated polymer of the invention.

A salt of a conjugated polymer of this invention is formed between an acid and a basic group of the compound, such as an amino functional group, or a base and an acidic group of the compound, such as a carboxyl functional group. According to another embodiment, the compound is a pharmaceutically acceptable acid addition salt.

The term "pharmaceutically acceptable," as used herein, refers to a component that is, within the scope of sound medical judgment, suitable for use in contact with the tissues of humans and other mammals without undue toxicity, irritation, allergic response and the like, and are commensurate with a reasonable benefit/risk ratio. A "pharmaceutically acceptable salt" means any non-toxic salt that, upon administration to a recipient, is capable of providing, either directly or indirectly, a conjugated polymer of this invention. A "pharmaceutically acceptable counterion" is an ionic portion of a salt that is not toxic when released from the salt upon administration to a recipient.

Acids commonly employed to form pharmaceutically acceptable salts include inorganic acids such as hydrogen bisulfide, hydrochloric acid, hydrobromic acid, hydroiodic acid, sulfuric acid and phosphoric acid, as well as organic acids such as para-toluenesulfonic acid, salicylic acid, tartaric acid, bitartaric acid, ascorbic acid, maleic acid, besylic acid, fumaric acid, gluconic acid, glucuronic acid, formic acid, glutamic acid, methanesulfonic acid, ethanesulfonic acid, benzenesulfonic acid, lactic acid, oxalic acid, para-bromophenylsulfonic acid, carbonic acid, succinic acid, citric acid, benzoic acid and acetic acid, as well as related inorganic and organic acids. Such pharmaceutically acceptable salts thus include sulfate, pyrosulfate, bisulfate, sulfite, bisulfate, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephthalate, sulfonate, xylene sulfonate, phenylacetate, phenylpropionate, phenylbutyrate, citrate, lactate, β-hydroxybutyrate, glycolate, maleate, tartrate, methanesulfonate, propanesulfonate, naphthalene-1-sulfonate, naphthalene-2-sulfonate, mandelate and other salts. In one embodiment, pharmaceutically acceptable acid addition salts include those formed with mineral acids such as hydrochloric acid and hydrobromic acid, and especially those formed with organic acids such as maleic acid.

The pharmaceutically acceptable salt may also be a salt of a compound of the present invention having an acidic functional group, such as a carboxylic acid functional group, and a base. Exemplary bases include, but are not limited to, hydroxide of alkali metals including sodium, potassium, and lithium; hydroxides of alkaline earth metals such as calcium and magnesium; hydroxides of other metals, such as aluminum and zinc; ammonia, organic amines such as unsubstituted or hydroxyl-substituted mono-, di-, or tri-alkylamines, dicyclohexylamine; tributyl amine; pyridine; N-methyl, N-ethylamine; diethylamine; triethylamine; mono-, bis-, or tris-(2-OH—($C_1$-$C_6$)-alkylamine), such as N,N-dimethyl-N-(2-hydroxyethyl)amine or tri-(2-hydroxyethyl)amine; N-methyl-D-glucamine; morpholine; thiomorpholine; piperidine; pyrrolidine; and amino acids such as arginine, lysine, and the like.

Unless otherwise indicated, when a disclosed compound is named or depicted by a structure without specifying the stereochemistry and has one or more chiral centers, it is understood to represent all possible stereoisomers of the compound.

Conjugated Polymers of the Invention

It has now been discovered that conjugating an ATRA prodrug or an ATRA molecule to a polymer, for example PVA, through a hydrolytically degradable (hydrolysable) linker, for example an ester linkage, provides for a conjugated polymer suitable for the use in control-release formulation of ATRA.

In a first aspect, the present invention is a conjugated polymer, comprising a polymer and an all-trans retinoid acid (ATRA) prodrug covalently bound to the polymer by a hydrolysable linker L, or a pharmaceutically acceptable salt thereof. In example embodiments of the first aspect, the polymer comprises a repeat unit presented by structural formulas (I) or (II):

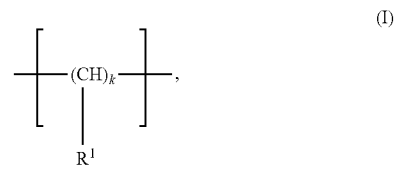

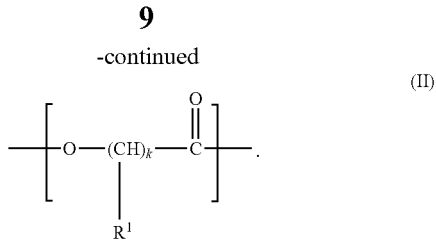

(II)

In an example embodiment of the first aspect, the ATRA prodrug is represented by structural formula (III):

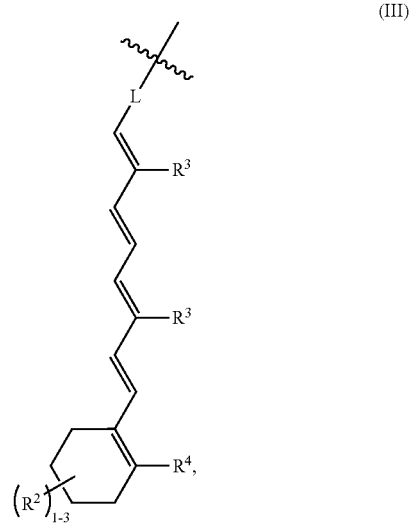

(III)

wherein hydrolysable linker L includes a substitutable atom of $R^1$.

In structural formulas (I) and (II), each $R^1$, independently, is $R^A$, a halogen, nitro, —$OR^A$, —$SR^A$, —$N(R^A)_2$, —$COOR^A$, —$OC(O)R^A$, —$C(O)R^A$, —$SO_4R^A$, —$PO_4(R^A)_2$. In an example embodiment, $R^1$ is —$OR^A$, —$SR^A$, —$N(R^A)_2$, —$COOR^A$, or —$OC(O)R^A$. In another example embodiment, $R^1$ is $R^{10}$, wherein $R^{10}$, for each occurrence independently, is a halogen, —$OR^C$, —$NHR^C$, or —$N(R^C)_2$. In yet another example, $R^1$ is —OH. The values and example values of variables L, $R^A$, $R^C$, $R^2$, $R^3$, and $R^4$ are as defined below with respect to various aspects of the present invention.

In an example embodiment of the first aspect, $R^A$ is, for each occurrence independently, hydrogen, a C1-C6 alkyl, or a C6-C18 aryl, optionally substituted with one or more groups selected from —OH, —$NH_2$, a C1-C3 (di)alkylamino, a halogen, —COOH, a C1-C4 alkoxy, and phenoxy. In another example, $R^A$ is, for each occurrence independently, hydrogen or a C1-C6 alkyl, optionally substituted with one or more groups selected from —OH, —$NH_2$, a C1-C3 (di)alkylamino, a halogen, —COOH, a C1-C4 alkoxy, and phenoxy. In another example, $R^A$, for each occurrence independently, is hydrogen or a C1-C6 alkyl, optionally substituted with one or more groups selected from —OH, —$NH_2$, and —COOH. In one example embodiment, $R^A$ is hydrogen. The values and example values of variables L, $R^C$, $R^1$, $R^2$, $R^3$, and $R^4$ are as defined above with respect to the first aspect and below with respect to various aspects of the present invention.

In example embodiment of the first aspect where $R^1$ is $R^{10}$, and $R^{10}$, for each occurrence independently is a halogen —$OR^C$, —$NHR^C$, or —$N(R^C)_2$, $R^C$, for each occurrence independently, is hydrogen or a C1-C6 alkyl, optionally substituted with one or more groups selected from —OH, —$NH_2$, and —COOH. For example, $R^C$ is, for each occurrence independently, hydrogen or a C1-C6 alkyl, optionally substituted with one or more groups selected from —OH, or —$NH_2$. In an example embodiment, $R^C$ is hydrogen. The values and example values of variables L, $R^A$, $R^1$, $R^2$, $R^3$, and $R^4$ are as defined above with respect to the first aspect and below with respect to various aspects of the present invention.

In an example embodiment of the first aspect, $R^2$, $R^3$, and $R^4$, each independently, is a halogen, —OH, —SH, —$NH_2$, —$NO_2$, —COOH, —$NHR^B$, —$SO_4H$, —$PO_4H_2$, —$PO_4HR^B$, $R^B$, —$OR^B$, —$SR^B)_2$, —$COOR^B$, —$OC(O)R^B$, —$C(O)R^B$, —$SO_4R^B$, or —$PO_4(R^B)_2$. For example, $R^2$, $R^3$, and $R^4$, each independently, is —OH, —SH, —$NH_2$, —$NHR^B$, —COOH, $R^B$, —$OR^B$, —$SR^B$, —$N(R^B)_2$, —COO$R^B$, —$OC(O)R^B$, or —$C(O)R^B$. In yet another example embodiment, $R^2$, $R^3$, and $R^4$, each independently, is $R^D$, —$OR^D$, —$NHR^D$, —$N(R^D)_2$. In another example, $R^2$, $R^3$, and $R^4$, each independently, is a $R^D$. The values and example values of variables L, $R^A$, $R^B$, $R^C$, $R^D$, and $R^1$ are as defined above with respect to the first aspect and below with respect to various aspects of the present invention.

In the example embodiments of the first aspect, $R^B$ is, for each occurrence independently, a C1-C6 alkyl or a C6-C18 aryl, optionally substituted with one or more groups selected from —OH, —$NH_2$, a C1-C3 (di)alkylamino, a halogen, COOH, a C1-C4 alkoxy, and phenoxy. For example, $R^B$ is, for each occurrence independently a C1-C6 alkyl optionally substituted with one or more groups selected from —OH, —$NH_2$, and —COOH. In one example embodiment, $R^B$ is a C1-C4 alkyl, such as methyl. The values and example values of variables L, $R^A$, $R^C$, $R^1$, $R^2$, $R^3$, and $R^4$ are as defined above with respect to the first aspect and below with respect to various aspects of the present invention.

In example embodiment of the first aspect where $R^2$, $R^3$, and $R^4$, each independently, is $R^D$, —$OR^D$, —$NHR^D$, —$N(R^D)_2$, $R^D$, for each occurrence independently, is hydrogen or a C1-C6 alkyl, optionally substituted with one or more groups selected from —OH, —$NH_2$, and —COOH. For example, $R^D$ is, for each occurrence independently, hydrogen or a C1-C6 alkyl, optionally substituted with one or more groups selected from —OH, or —$NH_2$. In an example embodiment, $R^D$ is methyl or ethyl. The values and example values of variables L, $R^A$, $R^C$, $R^1$, $R^2$, $R^3$, and $R^4$ are as defined above with respect to the first aspect and below with respect to various aspects of the present invention.

In various embodiments of the first aspect of the invention, each k, independently, is 1, 2, 3, 4, 5, or 6. For example, each k is 1. In another example, each k is 2. The values and example values of variables L, $R^A$, $R^C$, $R^B$, $R^D$, $R^1$, $R^2$, $R^3$, and $R^4$ are as defined above with respect to the first aspect and below with respect to various aspects of the present invention.

In an example embodiment of the first aspect of the invention, a hydrolysable linker L is a moiety selected from —C(O)O—, —OC(O)—, —NR*C(O)—, —C(O)NR*—, —(C═N—N(R*)$_2$)—, —OC(O)NR*—, —NR*C(O)O—, —OC(O)NR*NR*—, and —O—. Group R*, for each occurrence independently, is hydrogen or a C1-C4 alkyl.

In a second aspect, the present invention is a conjugated polymer, comprising a polymer and an all-trans retinoid acid (ATRA) prodrug covalently bound to the polymer by a hydrolysable linker L, or a pharmaceutically acceptable salt thereof. The polymer comprises a repeat unit presented by structural formulas (I) or (II), and the ATRA prodrug is represented by structural formula (III), as described above with respect to the first aspect. The hydrolysable linker L includes a substitutable atom of $R^1$. In the second aspect of the invention, each $R^1$, independently, is a halogen, $R^A$, $-OR^A$, $-SR^A$, $-N(R^A)_2$, $-COOR^A$, or $-OC(O)R^A$; and $R^2$, $R^3$, and $R^4$, each independently, is $-OH$, $-SH$, $-NH_2$, $-NHR^B$, $-COOH$, $R^B$, $-OR^B$, $-SR^B$, $-N(R^B)_2$, $-COOR^B$, $-OC(O)R^B$, or $-C(O)R^B$. The values and example values of variables L, R*, $R^A$, and $R^B$ are as defined above with respect to the first aspect and below with respect to various aspects of the present invention. In an example embodiment of the second aspect, $R^A$ is, for each occurrence independently, hydrogen or a C1-C6 alkyl, optionally substituted with one or more groups selected from $-OH$, $-NH_2$, and $-COOH$, while values of variables L, $R^B$ and, R* are as defined above with respect to the first aspect and below with respect to various aspects of the present invention. In another example of the second aspect, $R^B$ is, for each occurrence independently a C1-C6 alkyl optionally substituted with one or more groups selected from $-OH$, $-NH_2$, and $-COOH$, while values of variables L, $R^A$, and R* are as defined above with respect to the first aspect and below with respect to various aspects of the present invention.

In a third aspect, the present invention is a conjugated polymer, comprising a polymer and an all-trans retinoid acid (ATRA) prodrug covalently bound to the polymer by a hydrolysable linker L, or a pharmaceutically acceptable salt thereof. The polymer comprises a repeat unit presented by structural formulas (I) or (II), and the ATRA prodrug is represented by structural formula (III), as described above with respect to the first aspect. The hydrolysable linker L includes a substitutable atom of $R^1$. In the third aspect, the hydrolysable linker L is a moiety selected from $-C(O)O-$, $-OC(O)-$, $-NR*C(O)$, or $-C(O)NR*-$. Group R*, for each occurrence independently, is hydrogen or a C1-C4 alkyl. The values and example values of variables $R^A$, $R^C$, $R^B$, $R^D$, $R^1$, $R^2$, $R^3$, and $R^4$ are as defined above with respect to the first and second aspect aspects and below with respect to various aspects of the present invention.

In a fourth aspect, the present invention is a conjugated polymer, comprising a polymer and an all-trans retinoid acid (ATRA) prodrug covalently bound to the polymer by a hydrolysable linker L, or a pharmaceutically acceptable salt thereof. The ATRA prodrug is represented by structural formula (III), as described above with respect to the first aspect. In the fourth aspect, he polymer comprises a repeat unit represented by structural formulas (IA):

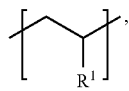

(IA)

the hydrolysable linker L includes a substitutable atom of $R^1$. The values and example values of variables L, R*, $R^A$, $R^C$, $R^B$, $R^D$, $R^1$, $R^2$, $R^3$, and $R^4$ are as defined above with respect to the first, second, and third aspects and below with respect to various aspects of the present invention.

In the fifth aspect, the present invention is a conjugated polymer, comprising a polymer and an all-trans retinoid acid (ATRA) prodrug covalently bound to the polymer by a hydrolysable linker L, or a pharmaceutically acceptable salt thereof. The polymer comprises a repeat unit presented by structural formulas (I) or (II), as described above with respect to the first aspect, or structural formula (IA), as described with respect to the fourth aspect. The hydrolysable linker L includes a substitutable atom of $R^1$. In the fifth aspect, the ATRA prodrug is represented by structural formula (IV):

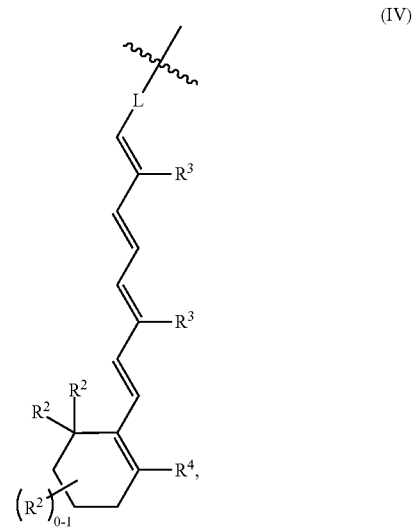

or a pharmaceutically acceptable salt thereof. The values and example values of variables L, R*, $R^A$, $R^C$, $R^B$, $R^D$, $R^1$, $R^2$, $R^3$, and $R^4$ are as defined above with respect to the first, second, third, and fourth aspects, and below, with respect to various aspects of the present invention.

In the sixth aspect, the present invention is a conjugated polymer, comprising a polymer and an all-trans retinoid acid (ATRA) prodrug covalently bound to the polymer by a hydrolysable linker L, or a pharmaceutically acceptable salt thereof. The polymer comprises a repeat unit presented by structural formulas (I) or (II), as described above with respect to the first aspect, or by structural formula (IA), as described with respect to the fourth aspect. The hydrolysable linker L includes a substitutable atom of $R^1$. In the sixth aspect, the ATRA prodrug is represented by structural formula (V):

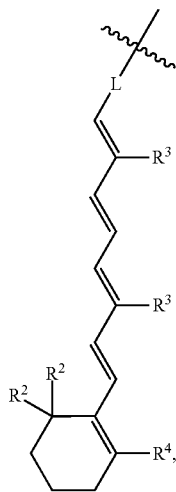

(V)

or a pharmaceutically acceptable salt thereof. The values and example values of variables L, $R^*$, $R^A$, $R^C$, $R^B$, $R^D$, $R^1$, $R^2$, $R^3$, and $R^4$ are as defined above with respect to the first, second, third, fourth, and fifth aspects, and below, with respect to various aspects of the present invention.

In the seventh aspect, the present invention is a conjugated polymer, comprising a polymer and an all-trans retinoid acid (ATRA) prodrug covalently bound to the polymer by a hydrolysable linker L, or a pharmaceutically acceptable salt thereof. In the seventh aspect, the polymer comprises a repeat unit represented by structural formula (IB):

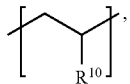

(IB)

and the hydrolysable linker L includes a substitutable atom of $R^1$ and the ATRA prodrug is represented by structural formula (V):

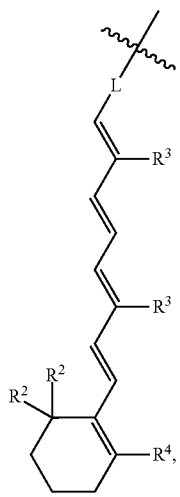

(V)

or a pharmaceutically acceptable salt thereof.

In the seventh aspect, $R^{10}$, for each occurrence independently, is a halogen, $-OR^C$, $-NHR^C$, or $-N(R^C)_2$. For example, $R^{10}$ is a halogen or $-OR^C$. In various example embodiments of the seventh aspect, the values and example values of variables L, $R^*$, $R^B$, $R^C$, $R^D$, $R^2$, $R^3$, and $R^4$ are as defined above with respect to the first, second, third, fourth, fifth, and sixth aspects, and below, with respect to various aspects of the present invention. In one example embodiment, $R^2$, $R^3$, and $R^4$, each independently, is $R^D$, $-OR^D$, $-NHR^D$, $-N(R^D)_2$. For example, $R^2$, $R^3$, and $R^4$, each independently, is $R^D$. In another example embodiment, L is a moiety selected from $-C(O)O-$, $-OC(O)-$. In various example embodiment of the seventh aspect, $R^C$, for each occurrence independently, is hydrogen or a C1-C6 alkyl, optionally substituted with one or more groups selected from $-OH$ and $-NH_2$. For example, $R^C$ is hydrogen. In certain example embodiments of the seventh aspect, $R^D$, for each occurrence independently, is hydrogen or a C1-C6 alkyl, optionally substituted with one or more groups selected from $-OH$ and $-NH_2$. For example, $R^D$ is methyl or ethyl.

In the eighth aspect, the present invention, is a conjugated polymer, wherein the polymer is polyvinyl alcohol (PVA), and the ATRA prodrug is represented by structural formula (VII):

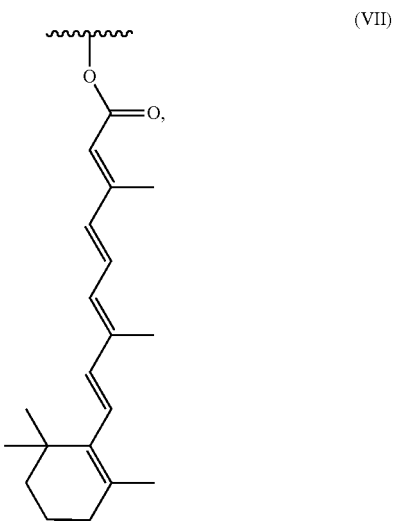

(VII)

or a pharmaceutically acceptable salt thereof.

In any of the aspects of the present invention, the polymer functionalization can range from about 1% to about 100%. For example, the polymer functionalization can be 5%, 10%, 15%, 20%, 25%, 30%, 35%, 40%, 45%, 50%, 55%, 60%, 65%, 70%, 75%, 80%, 85%, 90%, or 95%. In an example embodiment, the polymer functionalization is from about 10% to about 50%, for example, 10%.

Pharmaceutical Compositions

The invention also provides pharmaceutical compositions comprising an effective amount of a conjugated polymer described herein, or a pharmaceutically acceptable salt of said conjugated polymer; and a pharmaceutically acceptable carrier.

In one aspect, the present invention is a pharmaceutical composition comprising any of the conjugated polymers described herein, or a pharmaceutically acceptable salt of said conjugated polymer, in a pharmaceutically acceptable carrier, wherein the composition is an aqueous solution or a water-based cream. In one example, the pharmaceutical composition of the invention is suitable for topical administration.

Additional example embodiments of the pharmaceutical compositions of the present invention are described below.

Pharmaceutically acceptable carriers, adjuvants and vehicles that may be used in the pharmaceutical compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

If required, the solubility and bioavailability of the conjugated polymers of the present invention in pharmaceutical compositions may be enhanced by methods well-known in the art. One method includes the use of lipid excipients in the formulation. See "Oral Lipid-Based Formulations: Enhancing the Bioavailability of Poorly Water-Soluble Drugs (Drugs and the Pharmaceutical Sciences)," David J. Hauss, ed. Informa Healthcare, 2007; and "Role of Lipid Excipients in Modifying Oral and Parenteral Drug Delivery: Basic Principles and Biological Examples," Kishor M. Wasan, ed. Wiley-Interscience, 2006.

In example embodiments, the pharmaceutical compositions of the invention include those suitable for oral, rectal, nasal, topical (including buccal and sublingual), pulmonary, vaginal or parenteral (including subcutaneous, intramuscular, intravenous and intradermal) administration. In certain embodiments, the pharmaceutical compositions described herein can be administered transdermally (e.g., using a transdermal patch or iontophoretic techniques). Other formulations may conveniently be presented in unit dosage form, e.g., tablets, sustained release capsules, and in liposomes, and may be prepared by any methods well known in the art of pharmacy. See, for example, Remington's Pharmaceutical Sciences, Mack Publishing Company, Philadelphia, Pa. (17th ed. 1985).

Such preparative methods include the step of bringing into association with the conjugated polymer to be administered ingredients such as the carrier that constitutes one or more accessory ingredients. In general, the compositions are prepared by uniformly and intimately bringing into association the active ingredients with liquid carriers, liposomes or finely divided solid carriers, or both, and then, if necessary, shaping the product.

Topical administration of the pharmaceutical compositions of this invention is especially useful when the desired treatment involves areas or organs readily accessible by topical application. For application topically to the skin, the pharmaceutical composition can be formulated with the active components suspended or dissolved in a carrier. Carriers for topical administration of the compounds of this invention include, but are not limited to, mineral oil, liquid petroleum, white petroleum, propylene glycol, polyoxyethylene polyoxypropylene compound, emulsifying wax, and water. Alternatively, the pharmaceutical composition can be formulated with a suitable lotion or cream containing the active compound suspended or dissolved in a carrier. Suitable carriers include, but are not limited to, mineral oil, sorbitan monostearate, polysorbate 60, cetyl esters wax, cetearyl alcohol, 2-octyldodecanol, benzyl alcohol, and water. The pharmaceutical compositions of this invention may also be topically applied to the lower intestinal tract by rectal suppository formulation or in a suitable enema formulation. Topically-transdermal patches and iontophoretic administration are also included in this invention.

Various techniques can be used for providing the patient compositions at the site of interest, such as injection, use of catheters, trocars, projectiles, pluronic gel, stents, sustained drug release polymers.

Thus, according to yet another embodiment, a conjugated polymer of this invention may be incorporated into compositions for coating an implantable medical device, such as prostheses, artificial valves, vascular grafts, stents, or catheters. Suitable coatings and the general preparation of coated implantable devices are known in the art and are exemplified in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccharides, polyethylene glycol, phospholipids or combinations thereof to impart controlled release characteristics in the composition. Coatings for invasive devices are to be included within the definition of pharmaceutically acceptable carrier, adjuvant or vehicle, as those terms are used herein.

According to another embodiment, the invention provides a method of coating an implantable medical device comprising the step of contacting said device with the coating composition described above. It will be obvious to those skilled in the art that the coating of the device will occur prior to implantation into a patient.

According to another embodiment, the invention provides an implantable medical device coated with or impregnated with a compound or a composition comprising a conjugated polymer of this invention, such that said compound is therapeutically active.

Where an organ or tissue is accessible because of removal from the patient, such organ or tissue may be bathed in a medium containing a composition of this invention, a composition of this invention may be painted onto the organ, or a composition of this invention may be applied in any other convenient way.

In another embodiment, a composition of this invention further comprises a second therapeutic agent. In one embodiment, the second therapeutic agent is one or more additional conjugated polymers of the invention.

In another embodiment, the second therapeutic agent may be selected from any compound or therapeutic agent known to have or that demonstrates advantageous properties when administered with a conjugated polymer described herein.

For pharmaceutical compositions that comprise a second therapeutic agent, an effective amount of the second therapeutic agent is between about 20% and 100% of the dosage normally utilized in a monotherapy regime using just that agent. Preferably, an effective amount is between about 70% and 100% of the normal monotherapeutic dose. The normal monotherapeutic dosages of these second therapeutic agents are well known in the art. See, e.g., Wells et al., eds., Pharmacotherapy Handbook, 2nd Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000), each of which references are incorporated herein by reference in their entirety.

In certain embodiments, a conjugated polymer described herein is administered orally. Compositions of the present invention suitable for oral administration may be presented as discrete units such as capsules, sachets, or tablets each containing a predetermined amount of the active ingredient; a powder or granules; a solution or a suspension in an aqueous liquid or a non-aqueous liquid; an oil-in-water liquid emulsion; a water-in-oil liquid emulsion; packed in liposomes; or as a bolus, etc. Soft gelatin capsules can be useful for containing such suspensions, which may beneficially increase the rate of compound absorption.

In the case of tablets for oral use, carriers that are commonly used include lactose and corn starch. Lubricating agents, such as magnesium stearate, are also typically added. For oral administration in a capsule form, useful diluents include lactose and dried cornstarch. When aqueous suspensions are administered orally, the active ingredient is combined with emulsifying and suspending agents. If desired, certain sweetening and/or flavoring and/or coloring agents may be added.

Compositions suitable for oral administration include lozenges comprising the ingredients in a flavored basis, usually sucrose and acacia or tragacanth; and pastilles comprising the active ingredient in an inert basis such as gelatin and glycerin, or sucrose and acacia.

Compositions suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze dried (lyophilized) condition requiring only the addition of the sterile liquid carrier, for example water for injections, immediately prior to use. Extemporaneous injection solutions and suspensions may be prepared from sterile powders, granules and tablets.

Such injection solutions may be in the form, for example, of a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally-acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant.

The pharmaceutical compositions of this invention may be administered in the form of suppositories for rectal administration. These compositions can be prepared by mixing a conjugated polymer of this invention with a suitable non-irritating excipient which is solid at room temperature but liquid at the rectal temperature and therefore will melt in the rectum to release the active components. Such materials include, but are not limited to, cocoa butter, beeswax and polyethylene glycols.

The pharmaceutical compositions of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art. See, e.g.: Rabinowitz J D and Zaffaroni A C, U.S. Pat. No. 6,803,031, assigned to Alexza Molecular Delivery Corporation.

Methods of Treatment

The invention also includes methods treatment of diseases, disorders or pathological conditions comprising administering an effective amount of a conjugated polymer of the invention to a subject in need thereof. Diseases and conditions contemplated include those wherein modulation (inhibition or activation) of a Retinoic Acid Receptor (RAR) can have a therapeutically beneficial effect.

Without being limited to any particular theory, it is believed that RAR is a type of nuclear receptor which can also act as a transcription factor. There are three retinoic acid receptors: RAR-alpha, RAR-beta, and RAR-gamma. RAR heterodimerizes with RXR and, in the absence of ligand, the RAR/RXR dimer binds to hormone response elements known as retinoic acid response elements (RAREs) complexed with corepressor protein. Binding of agonist ligands to RAR results in dissociation of corepressor and recruitment of coactivator protein that, in turn, promotes transcription of the downstream target gene into mRNA and, eventually, protein.

Such diseases and conditions that can benefit from modulation of RAR include, but are not limited to: acne, psoriasis, rheumatoid arthritis, Kaposi's sarcoma, head and neck squamous cell carcinoma, ovarian carcinoma, bladder cancer, neuroblastoma, lymphoblastic leukemia, and acute promyelocytic leukemia (APL).

Kits

The present invention also provides kits for use to treat the target disease or disorder. These kits comprise (a) a pharmaceutical composition comprising a conjugated polymer described herein or a salt thereof, wherein said pharmaceutical composition is in a container; and (b) instructions describing a method of using the pharmaceutical composition to treat the target disease or disorder.

The container may be any vessel or other sealed or sealable apparatus that can hold said pharmaceutical composition. Examples include bottles, ampules, divided or multi-chambered holders bottles, wherein each division or chamber comprises a single dose of said composition, a divided foil packet wherein each division comprises a single dose of said composition, or a dispenser that dispenses single doses of said composition. The container can be in any conventional shape or form as known in the art which is made of a pharmaceutically acceptable material, for example a paper or cardboard box, a glass or plastic bottle or jar, a re-sealable bag (for example, to hold a "refill" of tablets for placement into a different container), or a blister pack with individual doses for pressing out of the pack according to a therapeutic schedule. The container employed can depend on the exact dosage form involved, for example a conventional cardboard box would not generally be used to hold a liquid suspension. It is feasible that more than one container can be used together in a single package to market a single dosage form. For example, tablets may be contained in a bottle, which is in turn contained within a box. In one embodiment, the container is a blister pack.

The kits of this invention may also comprise a device to administer or to measure out a unit dose of the pharmaceutical composition. Such device may include an inhaler if said composition is an inhalable composition; a syringe and needle if said composition is an injectable composition; a syringe, spoon, pump, or a vessel with or without volume markings if said composition is an oral liquid composition; or any other measuring or delivery device appropriate to the dosage formulation of the composition present in the kit.

In certain embodiment, the kits of this invention may comprise in a separate vessel of container a pharmaceutical composition comprising a second therapeutic agent, such as one of those listed above for use for co-administration with a conjugated polymer of this invention.

Exemplification

The Synthesis and Evaluation of a PVA-ATRA Polymer-Drug Conjugate (PATRA) for Topical Controlled Delivery of ATRA.

When hydrated, PATRA forms a nanoparticle micelle which is soluble in water and provides protection from UV degradation of ATRA. Release of ATRA from the polymer conjugate was sustained for up to ten days in vitro. Delivery into skin was evaluated first using explant pig dermis which showed a near four-fold increase in ATRA accumulation within the dermis and a ten-fold reduction in permeated ATRA after 12 hours compared to bolus ATRA administration. When tested in vivo PATRA was observed to elicit minimal inflammatory response compared to ATRA therapy, while remaining present for up to nearly five days post-application.

Materials and Methods

Materials

PVA and ATRA were purchased form Sigma-Aldrich (St. Louis, Mo.). Phosphate-buffered saline (PBS, 10×), Advanced-MEM, fetal bovine serum, antibiotic-antimycotic solution, and 100 mM L-Glutamine solution were purchased from Life Technologies (Grand Island, N.Y.). AlexaFluor 647 NHS ester was purchased from Life Technologies (Grand Island, N.Y.). NIH-3T3 cells were purchased from ATCC (Manassas, Va.).

Fabrication of PATRA 0.138 g DMAP and 1.0 g PVA were added to a stirred solution of ATRA (0.341 g) in 80 mL of anhydrous DMF/DMSO (later modified by using DMAc/5% LiCl). The reaction temperature was cooled to 0° C., and N,N'-dicyclohexycarbodiimide (DCC) was added to the reaction mixture. The reaction was allowed to run for 12-24 hours (depending on thin-layer chromatographic evaluation), during which the reaction temperature was allowed to reach room temperature. After the stipulated reaction period, DCU precipitate was filtered off, and the filtrate was concentrated in vacuo at low pressure, and precipitated in ether.

After centrifugation of the ether suspension at 5000 rpm for 15 minutes, the residue was collected, dissolved in water, and dialyzed against water for 12 h to remove any insoluble polar impurities. Lyophilization of the dialyzed product yielded yellowish PATRA conjugate. 1H NMR (400 MHz, D2O): 3.98-4.02 (m, —CH—OH, PVA), 1.5-2.25 (m, —CH2, PVA); 13C NMR (400 MHz, D2O): 64.71-67.68 (—CH2-CH—OH), 164.95 (CH—O—CO—).

In Vitro Analysis of PATRA

Release studies were carried out in a hydroalcoholic solution at two physiologically relevant temperatures, 20° C. and 37° C. The impact of ATRA on cell proliferation was assessed by supplementing the media of sub-confluent NIH-3T3 cells with ATRA, PATRA, PVA, and PBS in 24-well plates at concentrations equivalent to 10 µM ATRA. ATRA was prepared in a concentrated hydroalcoholic solution of 10 µL. A similar dose of ethanol (5 µL) was added to each treatment group immediately after addition of the testing agents. The cell number calculated from imaging of those wells is used as the reference in the calculation of relative cell density.

Uptake, retention, and penetration of ATRA in pig skin were investigated using a Franz diffusion cell as described and known in the art. Skin was harvested from the flanks of adult female Yorkshire pigs 1 hour after sacrifice with subcutaneous fat removed. Skin was sectioned and frozen at −80° C. for up to six months prior to use. Skin was prepared for diffusion experiments by thawing in PBS for one hour after which time all hair on the skin was shaven off. Test samples of skin were cut to 30 mm×30 mm square samples and placed into the diffusion cell such that the top of the dermis faced a 3 mL testing retention reservoir and the underside faced a 15 mL penetration reservoir. All studies were run at room temperature.

Samples were placed into the retention reservoir at a concentration of 0.1 mg/mL and followed for up to 12 hours. ATRA concentration was evaluated in both the retention and penetration reservoirs every four hours during this period via UV absorbance measurements. ATRA was first solubilized in a concentrated alcohol solution prior to being diluted into the retention well. A similar amount of ethanol was added to the PATRA retention well to control for ethanol concentration. For both groups, the penetration reservoir was filled with a hydroalcoholic solution so that the ATRA that could penetrate the skin would be soluble for UV absorbance measurement.

In Vivo PATRA Application

All animal studies were approved by the MIT Institutional Animal Care and Use Committee (IACUC). Animals were housed and cared for in the USDA-inspected MIT Animal Facility under federal, state, local, and NIH guidelines for animal care. Six week old Balb/CJ mice (n=18) were purchased from Jackson Laboratories (Bar Harbor, Me.). Mice were either used for irritation assessment or for IVIS PATRA retention testing.

Mice used for the assessment of irritation were given each of the two different treatments on 1 $cm^2$ regions of their dorsum, these included PATRA, ATRA, PVA, and PBS. A total of twelve mice were used in this assessment. 50 µL of 10 µM ATRA solution was placed on two 1 $cm^2$ shaved areas on the flanks of a Balb/CJ mouse on either side of midline. PATRA (0.092 mg $mL^{-1}$) and PVA (0.089 mg $mL^{-1}$) concentrations were controlled for 10 µM ATRA dosing. These solutions were rubbed into the skin using a cotton-tipped applicator for 30 seconds.

Mice used for PATRA retention testing were given two applications of one material, either PATRA or the unconjugated AF-647 dye, on two 1 $cm^2$ regions on their dorsum on midline. The material was allowed to adsorb into the skin for 30 minutes and then the mice were cleaned with a wetted towel to remove excess. Mice were imaged daily for up to seven days.

Histology

Tissues were fixed in zinc fixative without formalin for 48 hours. The excised tissues were cut on center and then embedded cut-face down in paraffin. Sections were taken at the wound center and at one further level of 500 µm reaching a total of 1 mm sampling length through the application site. At each level an H&E slide was stained. Unstained slides were also taken for potential IHC analysis of the tissue. All sections were 5 μm thick. Image analysis was performed using Image J.

Statistics

Statistical analysis was performed between groups using Student's t-test and rectified by ANOVA for comparisons between multiple groups. Values are represented as mean±S.D. A value of $p<0.05$ was used to indicate statistical significance.

Results

Chemical Synthesis of PVA Conjugated ATRA (PATRA)

Conjugating ATRA to a highly water soluble polymer through an ester-bond linkage, produced a water soluble polymer-drug conjugate for the controlled release of ATRA. The choice of polymer can determine the characteristics of the polymer conjugate. In particular, poly(vinyl alcohol) (PVA) functions as a topical glue that holds the polymer conjugate within the administration site for the controlled delivery of ATRA.

Conjugating ATRA to PVA was performed via the Steglich esterification process using DCC (N,N'-dicyclohexycarbodiimide) chemistry in a one-pot synthesis as described in FIG. 1. Initially, DMSO was used as solvent which resulted in a heterogeneous reaction condition for carrying out the esterification. This purified product was weighed and the UV absorbance for ATRA was quantified. It was determined that PVA functionalization with ATRA reached approximately 3.25 weight percent. It has also been found that the solubility of PVA can be increased by using DMAc/5% LiCl as the solvent system. Conjugation of ATRA to PVA was performed using DCC chemistry in DMF overnight at room temperature under nitrogen.

Conjugating the hydrophobic ATRA to the highly water-soluble PVA through an ester-bond linkage produces an amphiphilic material. In aqueous solution, the ATRA moieties along the PVA backbone attempt to isolate from the solvent, forming a micellar structure.

This increased water dispersion could be used to investigate new formulations and novel means of delivery into the target tissues. It is important to note here that micelles can be easily disrupted by non-specific interactions with proteins and other biomolecules; it would then be expected that while the PATRA may form a micelle in an uncluttered aqueous solution, it would lose this structure in vivo. Unlike emulsified formulations of ATRA, however, by covalently conjugating ATRA to the much larger PVA, along with PVAs mucoadhesive nature, the conjugated polymer can be retained within the application site to achieve controlled release of ATRA.

Figure 2:
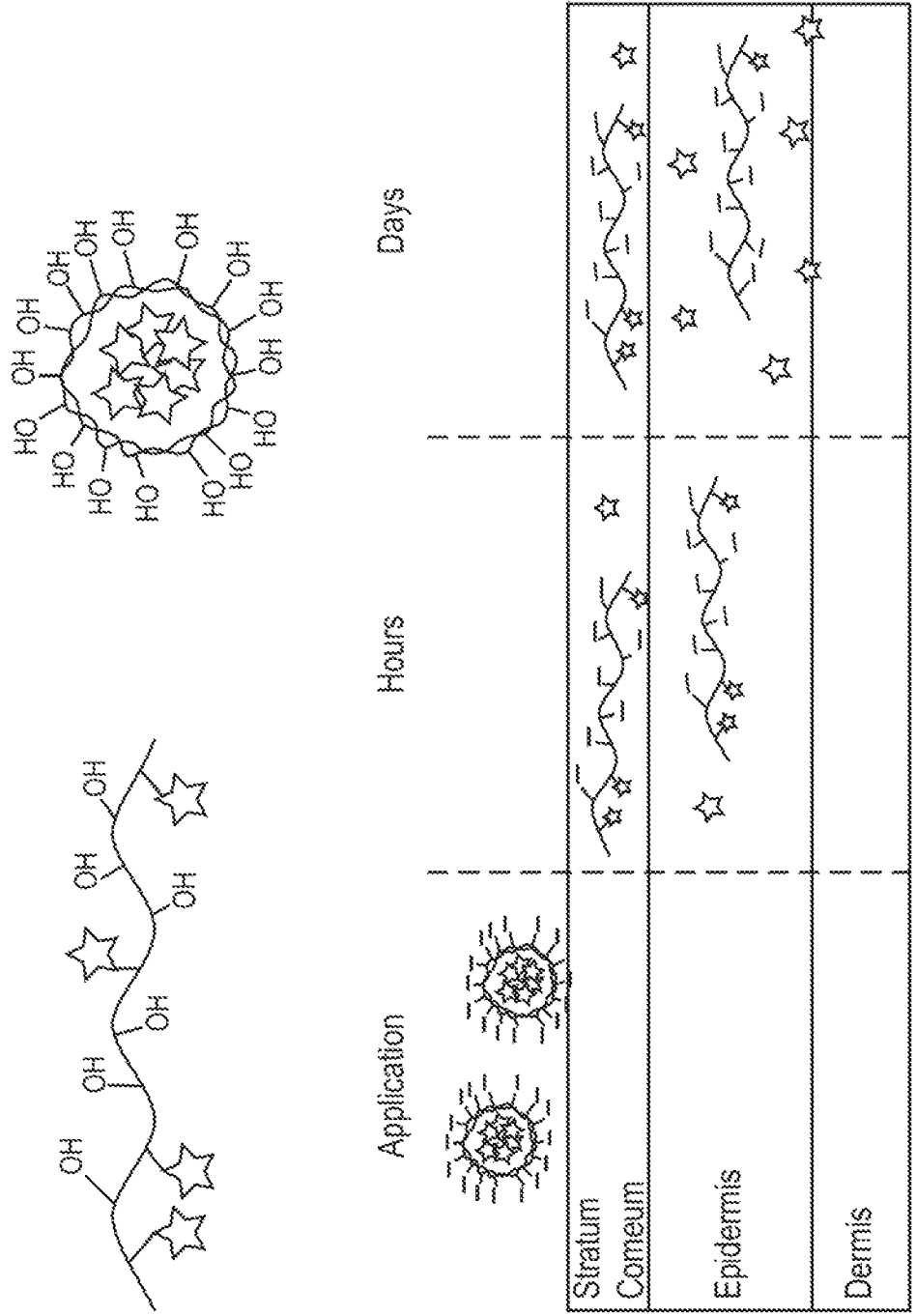
FIG. 2 is a schematic diagram showing the adsorption of micellar PATRA into the dermis.

FIG. 2 illustrates release of ATRA from the PATRA in the hydrated dermis.

Characterization of PATRA In Vitro

To investigate whether the covalent conjugation of ATRA to PVA would result in the creation of a water soluble drug-polymer conjugate that would naturally form a micellar structure in aqueous solution, a series of in vitro analyses on the PATRA molecule was performed. First, gross examination of the purified product was conducted, which was light yellow in color, a lighter shade than the pure ATRA product. PATRA was solubilized in water for ten minutes and then analyzed for the formation of nanoparticles as well as for its general appearance. The results are shown in FIGS. 3A and 3C. Nanoparticle structures were observed by dynamic light scattering (DLS) at concentrations starting at 50 mg/mL and lower. These particles were in the range of 120 to 150 nm in diameter. The appearance of these particles containing solutions was a light yellow, and was observed to vary in intensity with the relative dilution of the PATRA.

To investigate the nature of the aqueous solution of PATRA, transmission electron microscopy of the PATRA was performed using uranyl acetate negative staining to mark the hydrophobic ATRA-rich regions of the structure, which appear dark in the TEM micrographs (FIG. 3B). A nano-fibular structure was observed, where ATRA is occluded in the center of a thin fiber. These fiber structures are high aspect ratio structures, with only a few nanometers in diameter, while being tens of nanometers in length. These nano-fibers are seen to agglomerate into particles that are similar in size to the 120 to 150 nm structures we observed by DLS measurement.

As the PATRA polymer appeared to better solubilize the ATRA molecule in water, the extent of this increased solubility was determined by investigating the solubility of free ATRA and PATRA in three different solutions: (1) hydroalcoholic (50:50), (2) deionized water, and (3) PBS 1× (pH7.4). Solubility was evaluated by bringing 2 mg/ml of ATRA either free or conjugated to PVA into equilibrium at room temperature for 1 hour, followed by centrifugation of the solution at 1,500 rpm for five minutes to remove undissolved precipitate. The results are summarized in FIG. 3D. The supernatant from this process was then used for the testing of ATRA concentration via UV absorbance as previously described.

ATRA was observed to be insoluble in deionized water and PBS solutions; however, PATRA was observed in significant quantities in these solutions. PATRA was seen to carry approximately 0.33±0.08 mg/mL ATRA stably into deionized water and 0.35±0.04 mg/mL into PBS. These quantities were notably less than what we had previously observed from our solubility studies, suggesting that those findings may have included material that was able to be removed by centrifugation. These materials could include partially solubilized polymers as well as large micro-aggregates of the micelles.

The relative stability of the micelle structure was also investigated by evaluating it in simulated body fluids. This was accomplished by the addition of 5% fetal bovine serum (FBS) into deionized water or PBS solutions of PATRA. A complete loss of the particle signal was observed within the solution, generating a wide heterogeneous signal that was uninterpretable by DLS. This suggests that the presence of the proteins within the FBS could drive the disassembly of the micelle structure. A similar loss of particle structure was observed with the addition of ethanol to PATRA solubilized in water. By DLS, the particle distribution was very broad from multiple microns to tens of nanometers in scale for PATRA in the hydroalcoholic solution.

Controlled Release of ATRA

Release of ATRA from the PATRA polymer was evaluated by dialysis. The PVA polymer is 10 kDa and the ATRA molecule is only 300 Da; therefore, carrying out the release of ATRA within a dialysis bag with a 10 kDa cutoff enabled retention of the PATRA and PVA while isolating the ATRA. Release was carried out in hydroalcohol solution as this solvent mixture created a similar loss of particle structure as what would be hypothesized to happen in vivo and solubilizes the released ATRA. Tracking ATRA release in situ was therefore continued.

Figure 4B:
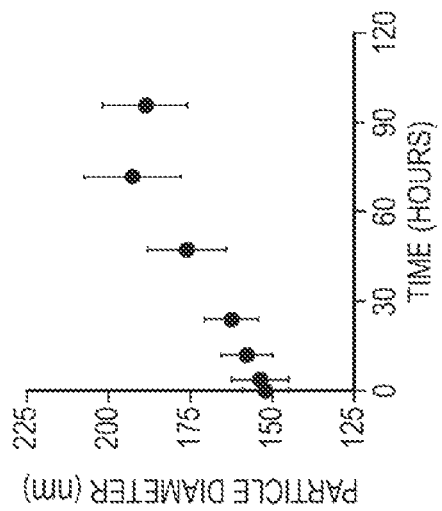
FIG. 4 presents plots illustrating controlled release of ATRA from PATRA and changes in particle size: (A) ATRA release followed daily at 20° C. and at 37° C. in hydroalcoholic solution out to two weeks; (B) Average particle size after degrading in water for specified periods of time (data shown is mean±S.D., n=3).
Figure 4A:
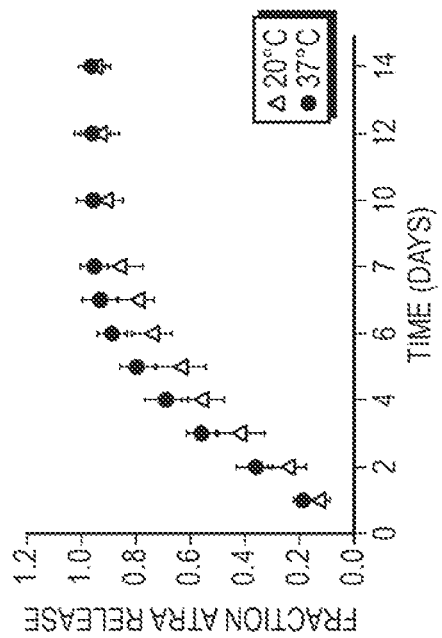

Release studies were carried out at two physiologically relevant temperatures as it is known that ester hydrolysis is affected by temperature. Temperatures of 20° C. and 37° C. were chosen as these would approximately represent room temperature and body temperature for the application of the PATRA formulation. Daily measurements of the released ATRA demonstrated a continuous liberation of the ATRA into solution over approximately eight days. The results are shown in FIG. 4A.

The in vitro stability of the PATRA micelles in water was then evaluated, as storage of the formed micelles in water would likely lead to the release of the ATRA. This evaluation was performed by solubilizing PATRA within deionized water and evaluating the average particle diameter over time. It was observed that the average particle diameter increased with storage significantly over a 100 hour study period. During this time it was also observed that the size distribution of particles widened. The results are shown in FIG. 4B.

In Vitro Activity of PATRA

The in vitro activity of ATRA was measured by evaluating its effect as an anti-proliferative, using the techniques well known in the art. This was done by supplementing the media of sub-confluent NIH-3T3 cells with ATRA, PATRA, PVA, and control solution in 24-well plates at concentrations equivalent to 10 µM ATRA. ATRA is not soluble in water, and as such must be solubilized in a concentrated hydroalcoholic solution which is then added to cell culture. Ethanol, even in a very low concentration, can be detrimental to cell survival and proliferation. For this reason a similar dose of ethanol was added to each treatment group immediately after addition of the testing agents. The control solution is deionized water with a small control volume of ethanol, and the cell number calculated from imaging of those wells is used as the reference in the calculation of relative cell density.

Cell proliferation was measured by daily brightfield phase contrast imaging for up to four days as well as with metabolic activity assay after the four days in culture. PATRA was observed to achieve a similar decrease in proliferation as ATRA, while PVA treatment caused negligible changes in proliferation. The results are presented in FIG. 5A and FIG. 5B. The level of anti-proliferative activity observed in PATRA treated cultures suggests that the activity of ATRA in vitro is not inhibited by its conjugation to PVA. It is also possible that PATRA may operate in a different fashion than free ATRA. A third option is that in the presence of cells, hydrolysis of the PATRA ester bond may be accelerated, liberating bound ATRA.

In Vitro Delivery of PATRA

Uptake, retention, and penetration of ATRA in pig skin were investigated using a Franz diffusion cell using previously described. In brief, skin was harvested from the flanks of adult female Yorkshire pigs 1 hour after sacrifice with subcutaneous fat removed. Skin was sectioned and frozen at −80° C. for up to six months prior to use. Skin was prepared for diffusion experiments by thawing in PBS for one hour after which time all hair on the skin was shaven off. Test samples of skin were cut to 30 mm×30 mm square samples that were placed into the diffusion cell such that the top of the dermis was pointed to a 3 mL testing retention reservoir and the underside towards a 15 mL penetration reservoir. All studies were run at room temperature.

Samples to be tested were placed into the retention reservoir at a concentration of 0.1 mg/mL and followed for up to 12 hours. ATRA concentration was evaluated in both the retention and penetration reservoirs every four hours during this period via UV absorbance measurements. Similar to what had been done for in vitro studies; ATRA was first solubilized in a concentrated alcohol solution prior to being diluted into the retention well. A similar amount of ethanol was added to the PATRA retention well to control for this. For both groups the penetration reservoir was filled with a hydroalcoholic solution so that the ATRA that could penetrate the skin would be soluble for UV absorbance measurement.

Figure 6C:
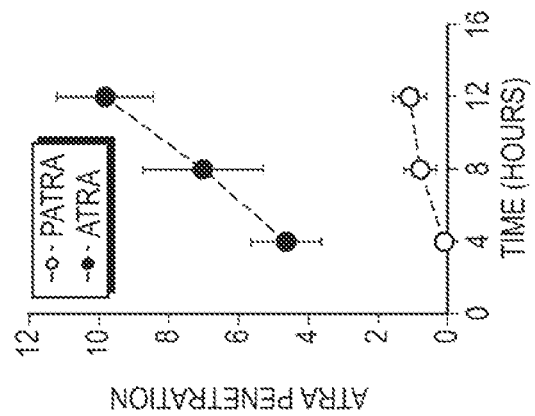
FIG. 6 presents data illustrating uptake and transport of ATRA in explant pig skin. (A) Histological appearance of pig dermis; (B) Uptake of fluorescently labeled PATRA after 4 and 12 hours of exposure (uptake is seen to significantly increase over this time and accumulate within the epidermis); (C) Fraction penetration of ATRA through pig dermis followed over 12 hours; (D) Quantification of fraction of ATRA accumulated within the pig dermis over 12 hours of exposure (data shown is mean±S.D., n=4).
Figure 6D:
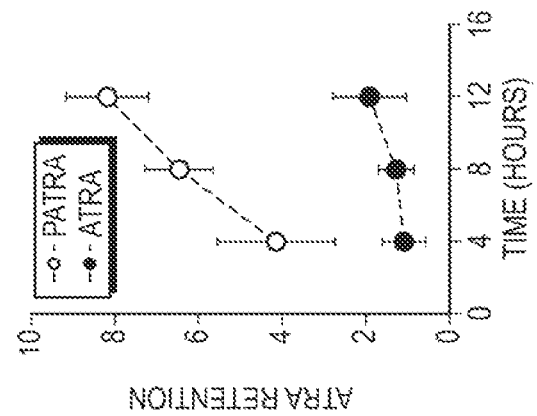
Figure 6A:
Figure 6B:
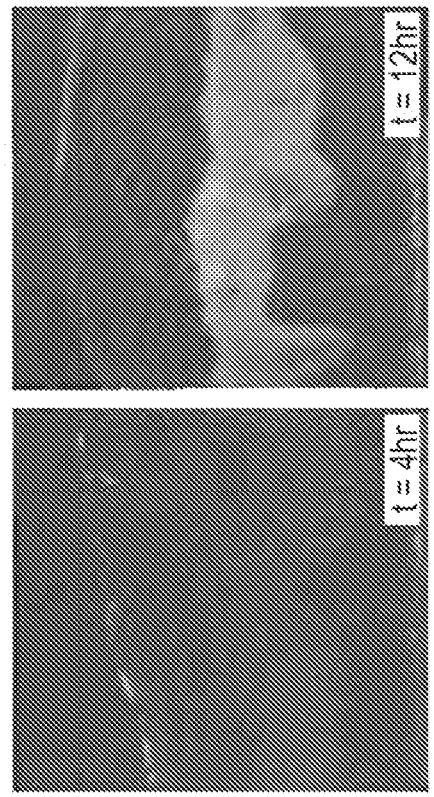

The structure of the pig skin is shown in FIG. 6A. The uppermost layer is the stratum corneum, followed by the epidermis and then the dermis. Each of these layers presents a different environment for ATRA and PATRA accumulation. The PATRA is labeled with a fluorescent dye to evaluate where within the skin the PATRA would localize. An increasing concentration of PATRA within the epidermis was observed over the testing period, as shown in FIG. 6B. After four hours the tissue looks largely unremarkable, with some fluorescent signal appearing in the stratum corneum. After 12 hours, an intense clear signal throughout the epidermis is observed, indicating a significant enrichment of this portion of the skin for the labeled PATRA.

Following the ATRA concentration within the receiving reservoir on the underside of the pig skin, we observed a much higher level of ATRA accumulation at every time point tested for free ATRA than PATRA, as illustrated in FIG. 6C, showing a plot of the fraction of ATRA penetrating the skin as a function of time.

Quantification of the ATRA concentration within the retention and penetration reservoirs allows performing a mass balance analysis for the ATRA in the testing system. This analysis showed that there was a significantly higher accumulation of the PATRA within the pig skin than was observed for free ATRA. This is illustrated in FIG. 6D, showing a plot for the fraction of ATRA accumulated within the treated skin sample. After 12 hours of exposure, approximately 8.2±1.1% of the ATRA placed in the retention reservoir had accumulated within the treated skin, with the amount increasing over the test period, compared to only 1.9±0.9% of free ATRA. This finding is in agreement with previous findings from labeled PATRA, in which accumulation within the epidermis over this period of time was observed.

In Vitro PARTA Causes Less Irritation Than ATRA

One of the most reported side effects of topical ATRA therapy is irritation within the application region. This is due in large part to the bolus administration of ATRA, which can often reach super-therapeutic levels easily, especially when treatments require multiple daily administrations of the ATRA formulation. To investigate the relative irritative nature of PATRA in comparison to ATRA, each was tested on the flanks of mice. Irritation was evaluated by digital imaging of the application site of ATRA, PATRA, or control solutions for up to five days post-application as well as by histological evaluation of inflammation after 5 days. In brief, 50 µL of 10 µM ATRA solution was placed on a 1 cm² shaved area on the flank of a Balb/CJ mouse. PATRA (0.092 mg mL$^{-1}$) and PVA (0.089 mg mL$^{-1}$) concentrations were controlled for 10 µM ATRA dosing. This solution is rubbed into the skin using a cotton-tipped applicator for 30 seconds. Each mouse received one of the four different material solutions applied in two locations. Inflammation and dermal changes subsequent to ATRA application were evaluated by both by digital imaging and by H&E histology.

Grossly, the ATRA treated skin begins to appear inflamed after three days, developing a thick and rough appearance. The results are shown in FIG. 7A. The stratum corneum thickens and has a crust like presentation, with flakes missing, giving a rash like appearance to the site application. The PATRA and PVA treated skin sections have no such change in appearance. After five days of treatment the ATRA treated skin looks less irritated with fewer red spots observed on the skin surface, however it still has a rash-like quality with a thick and calloused appearance. Neither the PATRA nor the PVA treated skin has any such changes. These application sites appear the same as they were prior to application and are very similar to control treated skin.

Histologically, the differences between the treatment groups can be easily appreciated, see FIG. 7B through 7D. Significantly increased stratum corneum (SC) and epidermal thickness was observed in ATRA treated mice, while not seen in PATRA or control group subjects, indicating increased inflammation within these tissues. In vivo evaluation of PATRA-induced irritation showed a significant reduction in both the irritation and inflammation as seen in similar ATRA applications. Without being limited to any particular theory, it is believed this is due to the controlled manner in which the ATRA is released from PATRA, reducing the likelihood of over-stimulating the dermis with ATRA upon administration.

Improved In Vivo Retention of PATRA

The application and retention of the PATRA material was followed using a dye-conjugated form of PATRA. This material was prepared similarly to the base PATRA with the inclusion of an alexafluor-647 dye that was bound to PVA through an ester-linkage, similar to the ATRA molecule. Whole-animal in vivo imaging for the tracking of the labeled conjugate was performed on a daily basis for seven days. As a control for the dye-conjugated PATRA, the free dye was similarly deposited on the dorsum of mice to track the loss of the free dye signal.

PATRA and the small molecule dye were both applied to the backs of mice in two locations on the midline on day 0. The materials were allowed to absorb into the skin for 30 minutes and then the backs of the mice were washed twice using a wet cloth. Average radiant efficiency was quantified within the area of application. The results are shown in FIGS. 8A and 8B. It was observed that the labeled PATRA showed a 3-fold longer half-life within the skin versus the unconjugated small molecule fluorescent dye. The signal from the dye-conjugated PATRA could be seen to persist for out to five days with the average time to 95% clearance lasting almost 6 days, as illustrated in the table shown in FIG. 8C.

Discussion

Topical application of all-trans retinoic acid is commonly used to treat severe acne and psoriasis as well as being used in many cosmetic applications for its anti-photoaging effect. Administration of ATRA however, presents many difficulties due to its hydrophobic nature and poor stability. A number of different approaches to delivering ATRA to the dermis have been previously investigated. These approaches have focused on formulating ATRA with emulsifiers and lipids to improve solubility or entrapping it within polymer-based particles to provide sustained release. Achieving both high solubility and controlled release of ATRA from a single platform is thus a challenging task.

A new approach to address these issues has now been discovered: direct conjugation of ATRA to PVA through a hydrolytically degradable ester-bond linkage. This conjugate formulation helps to solubilize ATRA in water while improving retention of the small molecule at the application site. The approach developed within this work is a simple and robust method using DCC chemistry to form a polymer-drug conjugate which provides a great deal of optimization flexibility in formulation design.

In vitro evaluation of ATRA release demonstrated sustained release for over ten days with little to no reduction in activity over that time. When hydrated, PATRA forms high aspect nano-fibers that agglomerate into larger submicron scale nanoparticles. Uptake and retention of the conjugated ATRA was significantly increased over the free ATRA for experiments using explant pig skin, and was observed to accumulate within the epidermal layer of the skin, increasing throughout the study period. Upon applying the PATRA conjugate in vivo, a significant reduction in gross inflammation compared to free ATRA was observed as well as a reduction in histological signs for inflammation. Further, the retention of PATRA within the application site was investigated, and it was demonstrated that this conjugated formulation was observed to be present at measurable levels for up to six days.

This data taken together presents a substantial argument for the capability of this described method to effectively control the delivery of ATRA into the dermis for topical applications. This style of approach may also be more broadly applicable for controlling ATRA delivery in combination with a number of existing formulations including emulsion and cream technologies. Self-assembled PATRA nano-fibers present beneficial properties for incorporation of ATRA in nanoparticle formulations for cancer therapy.

The teachings of all patents, published applications and references cited herein are incorporated by reference in their entirety.

EQUIVALENTS

While this invention has been particularly shown and described with references to example embodiments thereof, it will be understood by those skilled in the art that various changes in form and details may be made therein without departing from the scope of the invention encompassed by the appended claims.

What is claimed is:

1. A conjugated polymer, comprising:

a polymer; and an all-trans retinoid acid (ATRA) prodrug covalently bound to the polymer by a hydrolysable linker L, or a pharmaceutically acceptable salt thereof, wherein:

the polymer comprises repeat units presented by structural formula (IA) or (II):

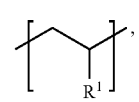

(IA)

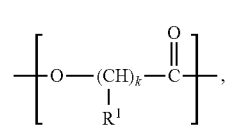

(II)

and
the ATRA prodrug is represented by structural formula (III):

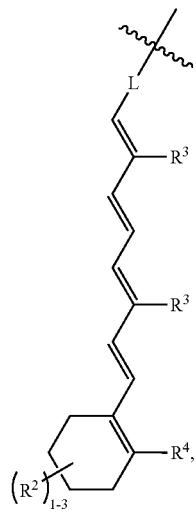

wherein:
the hydrolysable linker L is a moiety selected from —C(O)O—, —OC(O)—, —NR*C(O)—, —C(O)NR*—, —(C=N—N(R*)$_2$)—, —OC(O)NR*—, —NR*C(O)O—, —OC(O)NR*NR*—, and —O—, wherein R*, for each occurrence independently, is hydrogen or a C1-C4 alkyl;
each $R^1$, independently, is the ATRA prodrug, a halogen, nitro, —$OR^A$, —$SR^A$, —$N(R^A)_2$, —$COOR^A$, —OC(O)$R^A$, —C(O)$R^A$, —$SO_4R^A$, —$PO_4(R^A)_2$, wherein $R^A$ is, for each occurrence independently, hydrogen, a C1-C6 alkyl, or a C6-C18 aryl, optionally substituted with one or more groups selected from —OH, —NH$_2$, a C1-C3 (di)alkylamino, a halogen, —COOH, a C1-C4 alkoxy, and phenoxy;
$R^2$, $R^3$, and $R^4$, each independently, is a halogen, —OH, —SH, —NH$_2$, —NO$_2$, —COOH, —NHR$^B$, —SO$_4$H, —PO$_4$H$_2$, —PO$_4$HR$^B$, $R^B$, —OR$^B$, —SR$^B$, —N(R$^B$)$_2$, —OOR$^B$, —OC(O)R$^B$, —C(O)R$^B$, —SO$_4$R$^B$, —PO$_4$(R$^B$)$_2$, wherein $R^B$ is, for each occurrence independently, a C1-C6 alkyl or a C6-C18 aryl, optionally substituted with one or more groups selected from —OH, —NH$_2$, a C1-C3 (di)alkylamino, a halogen, COOH, a C1-C4 alkoxy, and phenoxy; and
each k, independently, is 1-6,
wherein about 10% to about 50% of the $R^1$ positions in the polymer are the ATRA prodrug.

2. The conjugated polymer of claim 1, wherein:
each $R^1$, independently, is the ATRA prodrug, a halogen, $R^A$, —$OR^A$, —$SR^A$, —$N(R^A)_2$, —$COOR^A$, —OC(O)$R^A$, wherein $R^A$ is, for each occurrence independently, hydrogen or a C1-C6 alkyl, optionally substituted with one or more groups selected from OH, NH$_2$, and —COOH; and
$R^2$, $R^3$, and $R^4$, each independently, is —OH, —SH, —NH$_2$, —NHR$^B$, —COOH, R$^B$, —OR$^B$, —SR$^B$, —N(R$^B$)2, —COOR$^B$, —OC(O)R$^B$, —C(O)R+, wherein R$^B$ is, for each occurrence independently a C1-C6 alkyl optionally substituted with one or more groups selected from OH, NH$_2$, and —COOH.

3. The conjugated polymer of claim 1, wherein L is a moiety selected from —C(O)O—, —OC(O)—, —NR*C(O)—, and —C(O)NR*—.

4. The conjugated polymer of claim 1, wherein the polymer comprises repeat units represented by structural formulas (IA):

or a pharmaceutically acceptable salt thereof.

5. The conjugated polymer of claim 1, wherein the ATRA prodrug is represented by structural formula (IV):

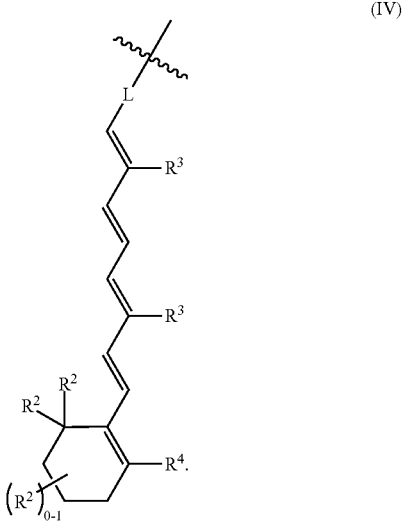

6. The conjugated polymer of claim 5, wherein the ATRA prodrug is represented by the following structural formula:

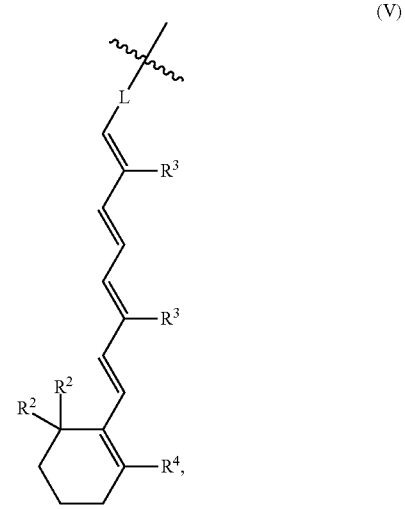

or a pharmaceutically acceptable salt thereof.

7. The conjugated polymer of claim 1, wherein the polymer comprises repeat units represented by structural formula (IA), wherein each $R^1$, independently, is the ATRA prodrug, a halogen, —$OR^C$, —$NHR^C$, or —$N(R^C)_2$; and the ATRA prodrug is represented by structural formula (VI):

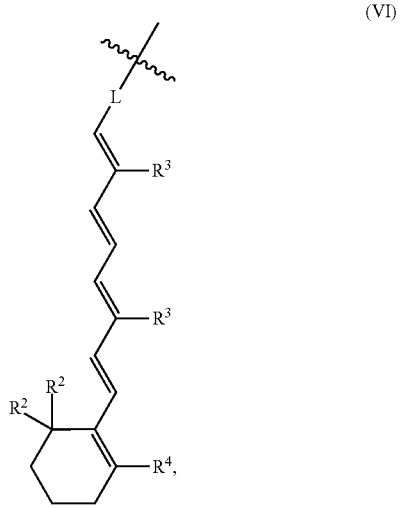

(VI)

or a pharmaceutically acceptable salt thereof, wherein:

$R^2$, $R^3$, and $R^4$, each independently, is $R^D$, —$OR^D$, —$NHR^D$, or —$N(R^D)_2$; and L is a moiety selected from —C(O)O—, —OC(O)—, wherein $R^C$ and $R^D$, for each occurrence independently, is hydrogen or a C1-C6 alkyl, optionally substituted with one or more groups selected from —OH, —$NH_2$, and —COOH.

8. The conjugated polymer of claim 7, wherein the ATRA prodrug is represented by structural formula (VII):

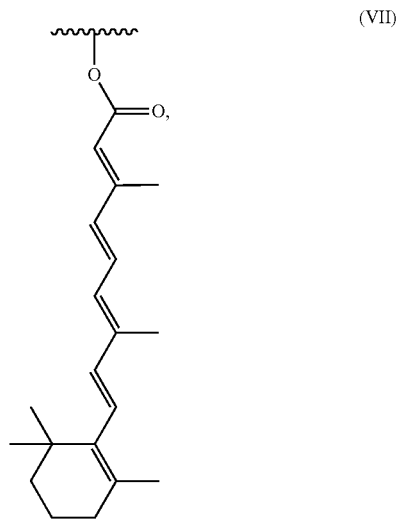

(VII)

or a pharmaceutically acceptable salt thereof.

9. The conjugated polymer of claim 1, wherein 10% of the $R^1$ positions in the polymer are the ATRA prodrug.

10. A pharmaceutical composition, comprising:
a conjugated polymer of claim 1 in pharmaceutically acceptable carrier.

11. The pharmaceutical composition of claim 10, wherein the composition is an aqueous solution or a water-based cream.

12. A method of treating a disorder in a subject in need thereof, comprising:
administering to the subject an effective amount of a conjugated polymer of claim 1 or a pharmaceutically acceptable salt thereof,
wherein the disorder is selected from acne, psoriasis, rheumatoid arthritis, Kaposi's sarcoma, head and neck squamous cell carcinoma, ovarian carcinoma, bladder cancer, neuroblastoma, lymphoblastic leukemia, and acute promyelocytic leukemia (APL).

13. A method of treating a disorder in a subject in need thereof, comprising:
topically administering to the subject an effective amount of a conjugated polymer of claim 1 or a pharmaceutically acceptable salt thereof,
wherein the disorder is selected from acne, psoriasis, and lymphoblastic leukemia.

14. The conjugated polymer of claim 1, wherein:
each $R^1$ independently is the ATRA prodrug, a halogen, —$OR^A$, —$SR^A$, —$N(R^A)_2$, —$COOR^A$, or —$OC(O)R^A$, wherein $R^A$ is, for each occurrence independently, hydrogen or a C1-C6 alkyl, optionally substituted with one or more groups selected from —OH, —$NH_2$, and —COOH; and $R^2$, $R^3$, and $R^4$, each independently, is —OH, —SH, —$NH_2$, —$NHR^B$, —COOH, $R^B$, —$OR^B$, —$SR^B$, —$N(R^B)_2$, —$COOR^B$, —$OC(O)R^B$, —$C(O)^{RB}$, wherein $R^B$ is, for each occurrence independently a C1-C6 alkyl optionally substituted with one or more groups selected from —OH, —$NH_2$, and —COOH.

15. A pharmaceutical composition, comprising:
a conjugated polymer of claim 8 in pharmaceutically acceptable carrier.

16. A pharmaceutical composition, comprising:
a conjugated polymer of claim 9 in pharmaceutically acceptable carrier.

17. A method of treating a disorder in a subject in need thereof, comprising:
administering to the subject an effective amount of a conjugated polymer of claim 8 or a pharmaceutically acceptable salt thereof,
wherein the disorder is selected from acne, psoriasis, rheumatoid arthritis, Kaposi's sarcoma, head and neck squamous cell carcinoma, ovarian carcinoma, bladder cancer, neuroblastoma, lymphoblastic leukemia, and acute promyelocytic leukemia (APL).

18. A method of treating a disorder in a subject in need thereof, comprising:
topically administering to the subject an effective amount of a conjugated polymer of claim 8 or a pharmaceutically acceptable salt thereof,
wherein the disorder is selected from acne, psoriasis, and lymphoblastic leukemia.

19. A conjugated polymer, comprising:
a polymer; and
an all-trans retinoid acid (ATRA) prodrug covalently bound to the polymer by a hydrolysable linker L,
or a pharmaceutically acceptable salt thereof,
wherein:
the polymer is PVA,
L is a moiety selected from —C(O)O—, —OC(O)—, and the ATRA prodrug is represented by structural formula (VII):

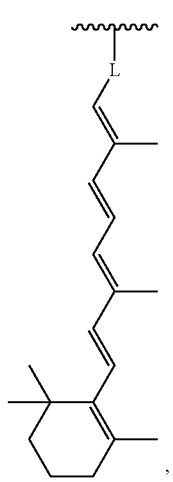

(VII)

, or a pharmaceutically acceptable salt thereof.

20. The conjugated polymer of claim 19, wherein about 10% to about 50% of the PVA monomers are covalently bound to the ATRA prodrug.

21. A conjugated polymer, comprising:
a polymer; and
an all-trans retinoid acid (ATRA) prodrug covalently bound to the polymer by a hydrolysable linker L, or a pharmaceutically acceptable salt thereof,
wherein:
the polymer comprises repeat units presented by structural formulas (IA) or (II):

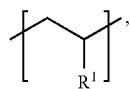

(IA)

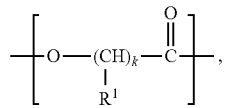

(II)

and
the ATRA prodrug is represented by structural formula (III):

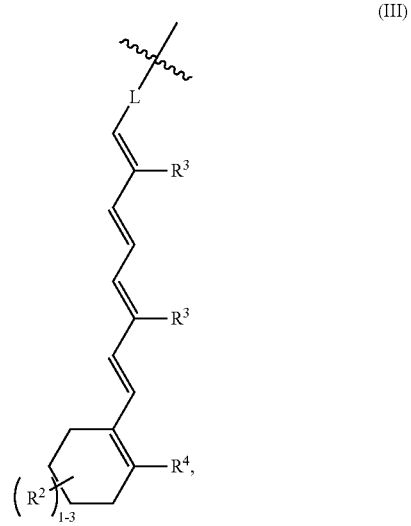

(III)

wherein:

the hydrolysable linker L is —C(O)O— or —OC(O)—;

each $R^1$, independently, is the ATRA prodrug or —OH $R^2$, $R^3$, and $R^4$, each independently, is a halogen, —OH, —SH, —NH$_2$, —NO$_2$, —COOH, —NHR$^B$, —SO$_4$H, —PO$_4$H$_2$, —PO$_4$HR$^B$, R$^B$, —OR$^B$, —SR$^B$, —N(R$^B$)$_2$, —OOR$^B$, —OC(O)R$^B$, —C(O)R$^B$, —SO$_4$R$^B$, —PO$_4$(R$^B$)$_2$, wherein R$^B$ is, for each occurrence independently, a C1-C6 alkyl or a C6-C18 aryl, optionally substituted with one or more groups selected from —OH, —NH$_2$, a C1-C3 (di)alkylamino, a halogen, COOH, a C1-C4 alkoxy, and phenoxy; and each k, independently, is 1-6, wherein about 10% to about 50% of the $R^1$ positions in the polymer are the ATRA prodrug.

* * * * *